(12) United States Patent
Ishihara et al.

(10) Patent No.: US 7,318,991 B2
(45) Date of Patent: Jan. 15, 2008

(54) HETEROCYCLE-BEARING ONIUM SALTS

(75) Inventors: Masami Ishihara, Kawagoe (JP); Yoji Urano, Kawagoe (JP); Masahiro Takahashi, Kawagoe (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 483 days.

(21) Appl. No.: 10/506,485

(22) PCT Filed: Oct. 11, 2002

(86) PCT No.: PCT/JP02/10605

§ 371 (c)(1),
(2), (4) Date: Sep. 2, 2004

(87) PCT Pub. No.: WO03/074509

PCT Pub. Date: Sep. 12, 2003

(65) Prior Publication Data

US 2005/0233253 A1 Oct. 20, 2005

(30) Foreign Application Priority Data

Mar. 4, 1922 (JP) ............................. 2002-056697

(51) Int. Cl.
- C08F 2/48 (2006.01)
- C07D 311/16 (2006.01)
- C07D 311/86 (2006.01)
- C07D 335/06 (2006.01)
- G03C 1/00 (2006.01)

(52) U.S. Cl. ..................... 430/270.1; 522/31; 549/23; 549/283; 549/392

(58) Field of Classification Search .............. 549/23, 549/283, 392; 430/270.1; 522/31, 37
See application file for complete search history.

(56) References Cited

U.S. PATENT DOCUMENTS

| | | | |
|---|---|---|---|
| 4,058,401 A | 11/1977 | Crivello | |
| 4,173,476 A | 11/1979 | Smith et al. | |
| 4,394,403 A | 7/1983 | Smith | |
| 4,683,317 A | 7/1987 | Crivello et al. | |
| 6,054,501 A | 4/2000 | Taniguchi et al. | |
| 6,528,232 B1 | 3/2003 | Maeda et al. | |

FOREIGN PATENT DOCUMENTS

| | | |
|---|---|---|
| EP | 0 889 361 A1 | 1/1999 |
| GB | 1 516 351 | 7/1978 |
| GB | 1 516 352 | 7/1978 |
| GB | 1 516 511 | 7/1978 |
| GB | 1 516 512 | 7/1978 |
| JP | 64-60098 | 3/1989 |
| JP | 64-67812 | 3/1989 |
| JP | 8-165290 | 6/1996 |
| JP | 9-012614 | 1/1997 |
| JP | 9-012615 | 1/1997 |
| JP | 10-101718 | 4/1998 |
| JP | 10-120766 | 5/1998 |
| JP | 10-130363 | 5/1998 |
| JP | 10-152554 | 6/1998 |
| JP | 10-168160 | 6/1998 |
| JP | 10-182634 | 7/1998 |
| JP | 10-182711 | 7/1998 |
| JP | 10-279616 | 10/1998 |
| JP | 10-330353 | 12/1998 |
| JP | 11-269169 | 10/1999 |
| JP | 11-322944 | 11/1999 |
| JP | 2001-294570 | 10/2001 |

OTHER PUBLICATIONS

Farhan et al. *Polish J.Chem.*, vol. 71, No. 9, pp. 1236-1245 (1997).
Abstract of JP 10-60098. "Energy ray curable composition and its cured material". Mar. 3, 1998.
Abstract of JP 10-67812. "Actinic-radiation-curing composition and cured product thereof", Mar. 10, 1998.

*Primary Examiner*—Bernard Dentz
(74) *Attorney, Agent, or Firm*—Hamre, Schumann, Mueller & Larson, P.C.

(57) ABSTRACT

The present invention relates to a heterocycle-containing onium salt useful as, for example, a cationic photopolymerization initiator and an acid generator for a chemically amplified resist, and provides "a heterocycle-containing onium salt shown in the specification.

18 Claims, 4 Drawing Sheets

HETEROCYCLE-BEARING ONIUM SALTS

TECHNICAL FIELD

The present invention relates to a heterocycle-containing onium salt useful as, for example, a cationic photopolymerization initiator and an acid generator for a chemically amplified resist.

BACKGROUND OF THE INVENTION

Recently, in the field of photopolymerization, a research on a cationic polymerization, instead of a radical polymerization, has been promoted to make polymerization easy even in the air without the effect of oxygen.

A cationic polymerization mainly uses as light source a high pressure mercury lamp or a metal halide lamp, including, for example, g-line (436 nm) and i-line (365 nm), and is widely known as a polymerization method for such as an epoxy compound and a vinyl ether compound, rather than a vinyl monomer.

As a cationic photopolymerization initiator, for example, sulfonium salt such as triarylsulfonium hexafluoroantimonate (see U.S. Pat. No. 4,058,401) and a 4-(phenylthio) phenyldiphenylsulfonium salt compound (see U.S. Pat. No. 4,173,476), and an iodonium salt such as diphenyliodonium hexafluorophosphate and diphenyliodonium hexafluoroantimonate (see JP-A-50-151996, JP-A-60-47029, etc.) have been known.

These compounds, however, have such problems of difficulty in preparing a polymer with high hardness when the said compounds are used as a cationic polymerization initiators, because use of a high pressure mercury lamp or a metal halide lamp as light source causes low acid generation efficiency.

Further, these sulfonium salts and onium salts are known to significantly reduce photocuring, when an inorganic strong acid such as hexafluorophosphate ($PF_6^-$) is used as a counter anion, compared with hexafluoroantimonate ($SbF_6^-$). However, use of $SbF_6^-$ may be inhibited in the future due to having strong toxicity.

Furthermore, Polish J. Chem., 71, p. 1236-1245 (1997) discloses 2-(phenyliodonio)xanthene-9-one tetrafluoroborate ($BF_4^-$) having a xanthonyl group at the cation moiety of the iodonium salt, and a synthesis example thereof. However, there is no disclosure that this compound can be used as a cationic polymerization initiator or not, and use of said compound as a cationic polymerization initiator could not obtain a polymer with sufficient hardness.

On the other hand, a high pressure mercury lamp or a metal halide lamp is widely used as exposure light source for such as a semiconductor resist, a liquid crystal resist, a solder resist for circuit board, PS (Pre-sensitized) plate and CTP (Computer To Plate) plate, and a sulfonium salt and an iodonium salt are also used as an acid generator for those applications.

However, these compounds have such problems that a resist with sufficiently high sensitivity cannot be provided due to low acid generation efficiency, when such as a high pressure mercury lamp or a metal halide lamp is used as light source.

Therefore, sulfonium salts with thioxanthone structure have been developed to provide high acid generation efficiency (see, for example, JP-A-8-165290, JP-A-9-12614, JP-A-9-12615, JP-A-10-60098, JP-A-10-67812, JP-A-10-101718, JP-A-10-120766, JP-A-10-130363, JP-A-10-152554, JP-A-10-168160, JP-A-10-182634, JP-A-10-182711, JP-A-10-279616, JP-A-11-269169 and JP-A-11-322944). However, because these sulfonium salts have absorption in the visible light region not shorter than 400 nm, and therefore show yellowish color. Thus use of these sulfonium salts as a polymerization initiator has such drawbacks that an obtained polymer has color under the influence of hue of said polymerization initiator itself, and therefore use of the said polymerization initiator as coating agents, adhesives or paints causes an obtained polymer with poor transparency and with hue which is different from desired hue.

Under the circumstance, development of an onium salt, providing sufficient hardening function even though $PF_6^-$ is used as a counter anion, and providing little effect on transparency of an obtained polymer, is required by research on a cation moiety with new structure providing high acid generation efficiency, even when such as a high pressure mercury lamp or a metal halide lamp is used as light source.

SUMMARY OF THE INVENTION

The present invention has been completed for the purpose of solving the above-mentioned problems and provides the following:

(1) A heterocycle-containing sulfonium salt shown by the general formula [1]:

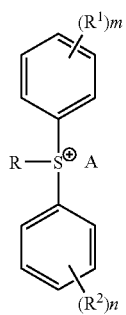

[wherein R is a group shown by the general formula [2]:

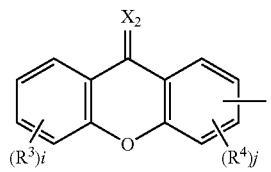

(wherein $R^3$ and $R^4$ are each independently a halogen atom, an alkyl group which may have a halogen atom or an aryl group as a substituent, or an aryl group which may have a halogen atom or a lower alkyl group as a substituent; $X_2$ is an oxygen atom or a sulfur atom; i is an integer of 0 to 4; and j is an integer of 0 to 3) or a group shown by the general formula [3]:

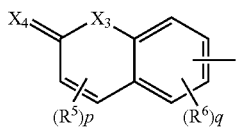

(wherein $R^5$ and $R^6$ are each independently a halogen atom, an alkyl group which may have a halogen atom or an aryl group as a substituent, or an aryl group which may have a halogen atom or a lower alkyl group as a substituent; $X_3$ and $X_4$ are each independently an oxygen atom or a sulfur atom; p is an integer of 0 to 2; and q is an integer of 0 to 3); $R^1$ and $R^2$ are each independently a halogen atom, an alkyl group which may have a halogen atom or an aryl group as a substituent, or an aryl group which may have a halogen atom or a lower alkyl group as a substituent; m and n are each independently an integer of 0 to 5; and A is a halogen atom or an anion derived from an inorganic strong acid, an organic acid or a compound shown by the general formula [4]:

$HM_1(R^7)_4$     [4]

(wherein $M_1$ is a boron atom or a gallium atom; and $R^7$ is an aryl group which may have a substituent selected from a lower haloalkyl group, a halogen atom, a nitro group and a cyano group)], (2) An iodonium salt shown by the general formula [35]:

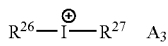

[wherein $R^{26}$ and $R^{27}$ are each independently an aryl group which may have a halogen atom or a lower alkyl group as a substituent, a group shown by the above-mentioned general formula [2] or a group shown by the above-mentioned general formula [3]; $A_3$ is a halogen atom or an anion derived from an inorganic strong acid, an organic acid or a compound shown by the general formula [4]; and provided that at least one of $R^{26}$ and $R^{27}$ is a group shown by the above-mentioned general formula [2] or [3] and when only one of $R^{26}$ and $R^{27}$ is a group shown by the above-mentioned general formula [2] or [3], $A_3$ is an anion derived from an inorganic strong acid shown by the general formula [36];

$HM_3F_6$     [36]

(wherein $M_3$ is a phosphorus atom, an arsenic atom or an antimony atom), an organic acid or a compound shown by the general formula [4]], (3) A cationic photopolymerization initiator, comprising a sulfonium salt shown by the general formula [8]:

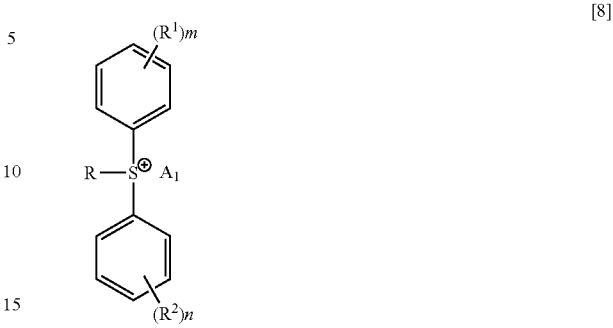

(wherein $A_1$ is an anion derived from an inorganic strong acid, a sulfonic acid or a compound shown by the general formula [4]; and R, $R^1$, $R^2$, m and n have the same meaning as above), (4) A cationic photopolymerization initiator, comprising an iodonium salt shown by the general formula [37]:

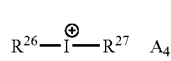

(wherein $A_4$ is an anion derived from an inorganic strong acid, a sulfonic acid or a compound shown by the general formula [4]; $R^{26}$ and $R^{27}$ have the same meaning as above; and provided that at least one of $R^{26}$ and $R^{27}$ is a group shown by the above-mentioned general formula [2] or [3] and when only one of $R^{26}$ and $R^{27}$ is a group shown by the above-mentioned general formula [2] or [3], an inorganic strong acid is one shown by the general formula [36]), (5) A method for polymerization of an epoxy monomer, which comprises using the polymerization initiator in the above-mentioned (3) and (4), (6) A method for polymerization of a vinyl ether monomer, which comprises using the polymerization initiator in the above-mentioned (3) and (4), (7) An acid generator for a resist, comprising a sulfonium salt shown by the general formula [9]:

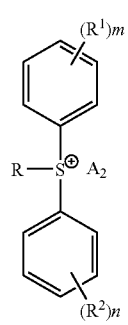

(wherein $A_2$ is an anion derived from an inorganic strong acid, an organic acid or a compound shown by the general formula [4]; and R, $R^1$, $R^2$, m and n have the same meaning as above), and (8) An acid generator for a resist, comprising an iodonium salt shown by the general formula [38]:

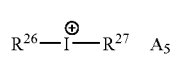

(wherein $A_5$ is an anion derived from an inorganic strong acid, an organic acid or a compound shown by the general formula [4]; $R^{26}$ and $R^{27}$ have the same meaning as above; and provided that at least one of $R^{26}$ and $R^{27}$ is a group shown by the above-mentioned general formula [2] or [3] and when only one of $R^{26}$ and $R^{27}$ is a group shown by the above-mentioned general formula [2] or [3], an inorganic strong acid is one shown by the general formula [36]).

The present inventors have conducted extensive study in order to realize the above-mentioned object and to arrive at the finding that a heterocycle-containing onium salt shown by the above-mentioned general formulae [1], [8], [9], [35], [37] and [38] has superior acid generation efficiency in wavelength region of a high pressure mercury lamp and a metal halide lamp, and good transparency in the visible light region (not shorter than 400 nm) (that is, little absorption in the visible light region), and thus they can be used as cationic photopolymerization initiators or acid generators not having the above-mentioned problems, or synthesis raw materials thereof, and finally the present invention has been completed on the basis of these findings.

Each curve code corresponds to result of each Example as yfollows:

–□–curve to Example 1

–◇–curve to Example 2

–△–curve to Example 3

–○–curve to Example 4

Figure 2:
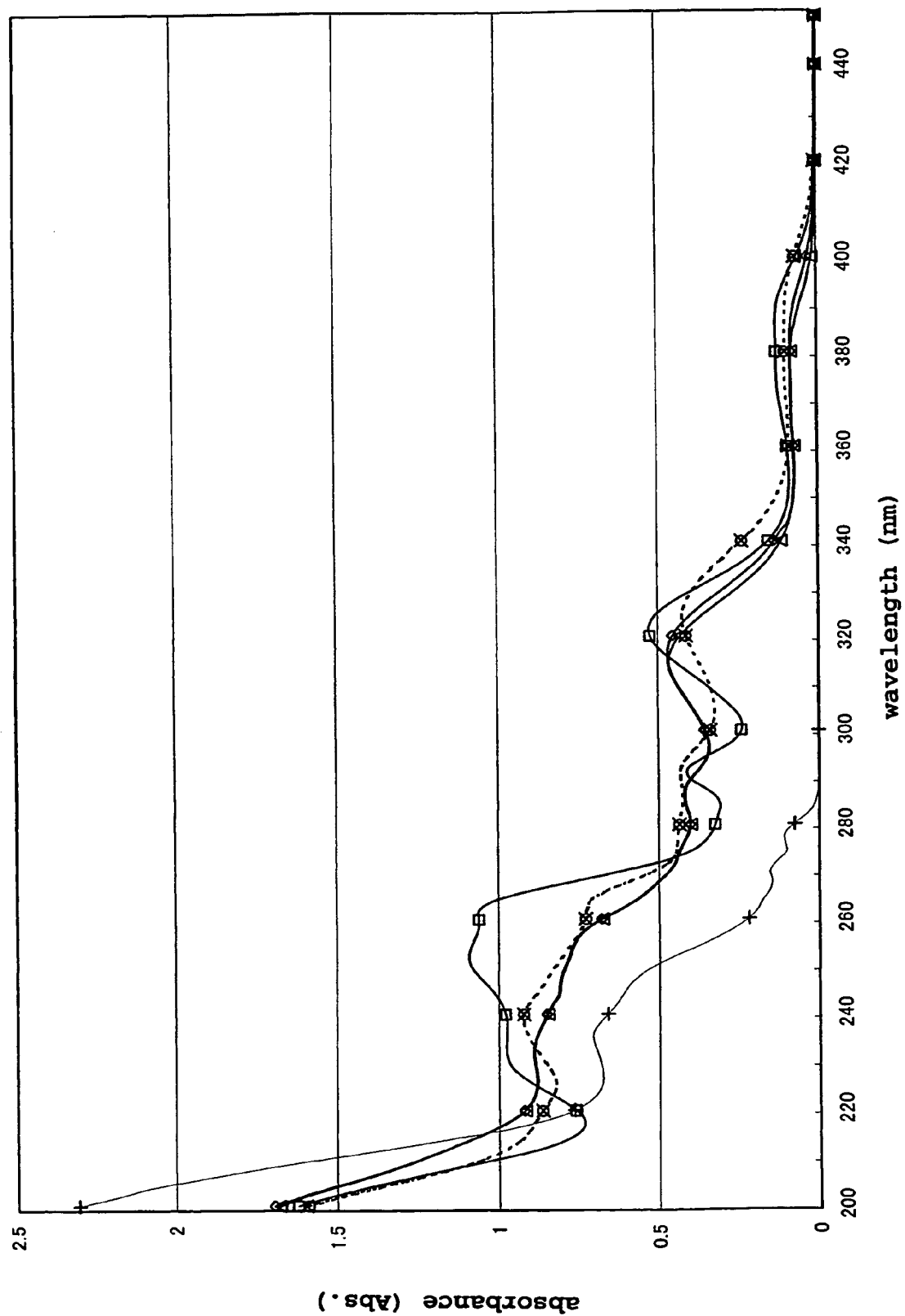

FIG. 2 shows UV-visible ray absorption spectra curves data on Comparative Examples 1 to 5 and Reference Example 1.

Each curve code corresponds to result of each Example as follows:

–◇–curve to Comparative Example 1

–△–curve to Comparative Example 2

–□–curve to Comparative Example 3

··×··curve to Comparative Example 4

··○··curve to Comparative Example 5

–+–curve to Reference Example 1

Figure 3:
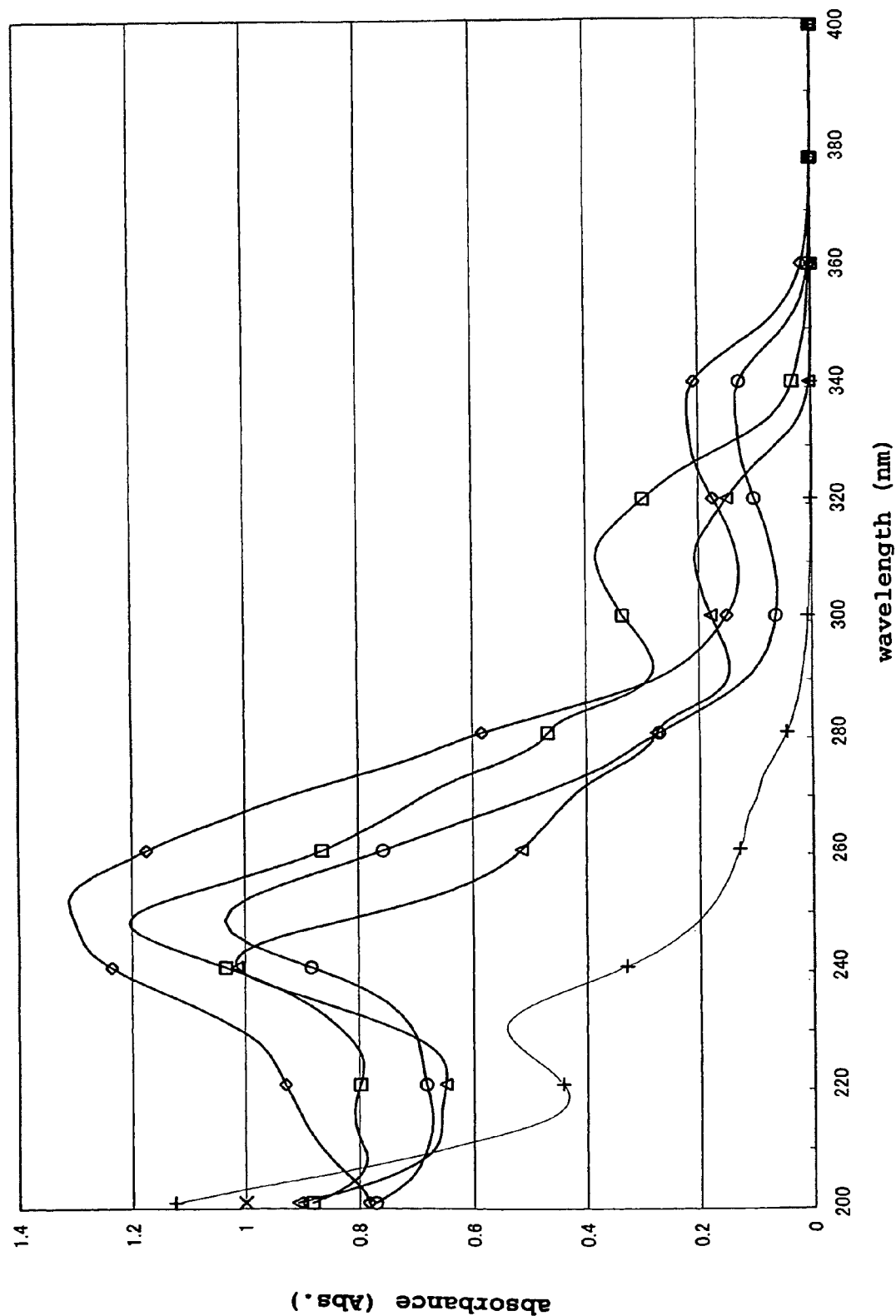

FIG. 3 shows UV-visible ray absorption spectra curves data on Examples 5 to 8, Comparative Example 6 and Reference Example 2.

Each curve code corresponds to result of each Example as follows:

–□–curve to Example 5

–◇–curve to Example 6

–△–curve to Example 7

–○–curve to Example 8

–×–curve to Comparative Example 6

–+–curve to Reference Example 2

Figure 4:
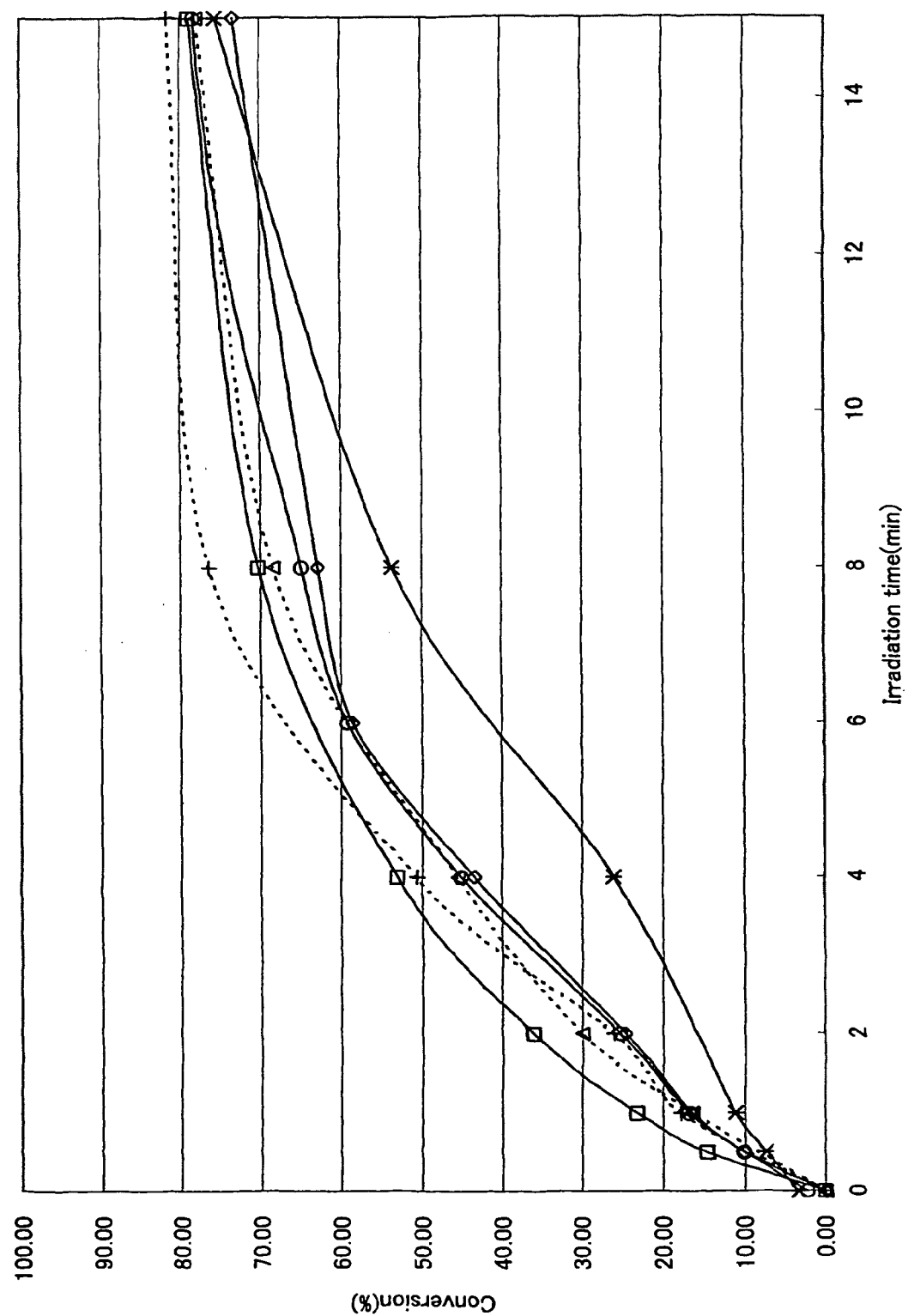

FIG. 4 shows UV-visible ray absorption spectra curves data on Examples 4 to 6 and 8 and Comparative Examples 2 and 3.

Each curve code corresponds to result of each Example as follows:

–□–curve to Example 4

–*–curve to Example 5

–◇–curve to Example 6

–○–curve to Example 8

··+··curve to Comparative Example 2

··△··curve to Comparative Example 3

BEST MODE FOR CARRYING OUT OF THE INVENTION

In the general formulae [1] to [3], [8] and [9], the halogen atom shown by $R^1$ to $R^6$ includes, for example, a fluorine atom, a chlorine atom, a bromine atom and an iodine atom, and among others, a chlorine atom is preferable.

The alkyl group of an alkyl group which may have a halogen atom or an aryl group as a substituent, shown by $R^1$ to $R^6$, may be straight chained, branched or cyclic, and includes one having generally 1 to 18, preferably 1 to 12 and more preferably 1 to 4 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a n-hexadecyl group, an isohexadecyl group, a sec-hexadecyl group, a tert-hexadecyl group, a neohexadecyl group, a n-heptadecyl group, an isoheptadecyl group, a sec-heptadecyl group, a tert-heptadecyl group, a neoheptadecyl group, a n-octadecyl group, an isooctadecyl group, a sec-octadecyl group, a tert-octadecyl group, a neooctadecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclohexadecyl group, a cycloheptadecyl group and a cyclooctadecyl group, and among others, a preferable one includes, for example, a methyl group, an ethyl group, a n-propyl group, an isopropyl group, a n-butyl group, an isobutyl group, a sec-butyl group and a tert-butyl group, and a more preferable one includes, for example, a methyl group and an ethyl group.

The halogen atom as the substituent of the above-mentioned alkyl group includes, for example, a fluorine atom, a chlorine atom, a bromine atom and an iodine atom, and among others, a chlorine atom is preferable.

The aryl group as the substituent of the above-mentioned alkyl group includes one having generally 6 to 16, preferably 6 to 14 carbon atoms, which is specifically exemplified by, for example, a phenyl group, a naphthyl group, an anthryl group, a phenanthrenyl group and a pyrenyl group, and among others, for example, a phenyl group, a naphthyl group, an anthryl group and a phenanthrenyl group are preferable.

In the general formulae [1] to [3], [8], [9], [35], [37] and [38], the aryl group of the aryl group which may have a halogen atom or a lower alkyl group as a substituent, shown by $R^1$ to $R^6$, $R^{26}$ and $R^{27}$ includes one having generally 6 to 16, preferably 6 to 14 carbon atoms, which is specifically exemplified by, for example, a phenyl group, a naphthyl group, an anthryl group, a phenanthrenyl group and a pyrenyl group, and among others, for example, a phenyl group, a naphthyl group, an anthryl group and a phenanthrenyl group are preferable.

The halogen atom as the substituent of the above-mentioned aryl group includes, for example, a fluorine atom, a chlorine atom, a bromine atom and an iodine atom, and among others, a chlorine atom is preferable.

The lower alkyl group as the substituent of the above-mentioned aryl group may be straight chained, branched or cyclic, and includes one having generally 1 to 6, preferably 1 to 4 carbon atoms, which is specifically exemplified by the same as examples of the alkyl group having 1 to 6 carbon atoms among the alkyl groups which may have a halogen atom or an aryl group as a substituent, shown by the above-mentioned $R^1$ to $R^6$, and among others, a preferable one includes, for example, a methyl group, an ethyl group, a n-propyl group, an isopropyl group, a n-butyl group, an isobutyl group, a sec-butyl group and a tert-butyl group, a more preferable one includes a methyl group and an ethyl group.

In the general formulae [2] and [3], $X_2$ to $X_4$ are each independently an oxygen atom and a sulfur atom, and among them, an oxygen atom is preferable.

In the general formulae [1], [8] and [9], m and n are each independently an integer of generally 0 to 5, preferably 0 to 2.

In the general formula [2], i is an integer of generally 0 to 4, preferably 0 to 2 and j is an integer of generally 0 to 3, preferably 0 to 2.

In the general formula [3], p is an integer of generally 0 to 2, preferably 0 to 1 and q is an integer of generally 0 to 3, preferably 0 to 2.

In the general formula [4], the aryl group of the aryl group which may have a substituent selected from a lower haloalkyl group, a halogen atom, a nitro group and a cyano group, shown by $R^7$ includes one having generally 6 to 16, preferably 6 to 14 carbon atoms, which is specifically exemplified by, for example, a phenyl group, a naphthyl group, an anthryl group, a phenanthrenyl group and a pyrenyl group, and among others, a phenyl group is preferable.

The lower haloalkyl group as the substituent of the aryl group shown by the above-mentioned $R^7$ may be straight chained, branched or cyclic, and includes one, wherein a part of or all of hydrogen atoms of the lower haloalkyl group having generally 1 to 6, preferably 1 to 4 carbon atoms are substituted by a halogen atom (e.g. a fluorine atom, a chlorine atom, a bromine atom and an iodine atom), which is specifically exemplified by, for example, a fluoromethyl group, a chloromethyl group, a bromomethyl group, an iodomethyl group, a difluoromethyl group, a dichloromethyl group, a dibromomethyl group, a diiodomethyl group, a trifluoromethyl group, a trichloromethyl group, a tribromomethyl group, a triiodomethyl group, a trifluoroethyl group, a trichloroethyl group, a tribromoethyl group, a triiodoethyl group, a pentafluoroethyl group, a pentachloroethyl group, a pentabromoethyl group, a pentaiodoethyl group, a heptafluoropropyl group, a heptachloropropyl group, a heptabromopropyl group, a heptaiodopropyl group, a nonafluorobutyl group, a nonachlorobutyl group, a nonabromobutyl group, a nonaiodobutyl group, a perfluoropentyl group, a perchloropentyl group, a perbromopentyl group, a periodopentyl group, a perfluorohexyl group, a perchlorohexyl group, a perbromohexyl group, a periodohexyl group, a trifluorocyclobutyl group, a trichlorocyclobutyl group, a tribromocyclobutyl group, a triiodocyclobutyl group, a tetrafluorocyclopentyl group, a tetrachlorocyclopentyl group, a tetrabromocyclopentyl group, a tetraiodocyclopentyl group, a pentafluorocyclohexyl group, a pentachlorocyclohexyl group, a pentabromocyclohexyl group and a pentaiodocyclohexyl group, and among others, a preferable one includes, for example, a trifluoromethyl group, a trichloromethyl group, a tribromomethyl group and a triiodomethyl group, and a more preferable one includes a trifluoromethyl group.

The halogen atom as the substituent of the aryl group shown by the above-mentioned $R^7$ includes, for example, a fluorine atom, a chlorine atom, a bromine atom and an iodine atom, and among others, a fluorine atom is preferable.

In the general formulae [1] and [35], the halogen atom shown by A and $A_3$ includes, for example, a fluorine atom, a chlorine atom, a bromine atom and an iodine atom, and among others, a chlorine atom and a bromine atom are preferable.

In the general formulae [1], [8], [9], [35], [37] and [38], the anion derived from the inorganic strong acid shown by A and $A_1$ to $A_5$ includes one derived from inorganic strong acids such as nitric acid, sulfuric acid, halosulfuric acid, perhalogenic acid and one shown by the general formula [5]:

$$HM_2F_k \qquad [5]$$

(wherein $M_2$ is a metalloid atom or a metal atom; and k is an integer of 4 or 6).

In the general formulae [35], [37] and [38], when only one of $R^{26}$ and $R^{27}$ is a group shown by the above-mentioned general formula [2] or [3], the ainion derived from the inorganic strong acid shown by $A_3$ to $A_5$ includes one derived from an inorganic strong acid shown by the general formula [36]:

$$HM_3F_6 \qquad [36]$$

(wherein $M_3$ is a phosphorus atom, an arsenic atom or an antimony atom).

In the general formula [5], the metalloid atom shown by $M_2$ includes, for example, a boron atom, a silicon atom, a phosphorus atom, an arsenic atom and an antimony atom, and among others, for example, a phosphorus atom, an arsenic atom and an antimony atom are preferable.

The metal atom shown by $M_2$ includes, for example, a titanium atom, a zirconium atom, an iron atom, a nickel atom, an aluminum atom and a gallium atom, and among others, a gallium atom is preferable.

In the general formulae [1], [9], [35] and [38], the anion derived from the organic acid and shown by A, $A_2$, $A_3$ and $A_5$ includes, for example, one derived from a sulfonic acid shown by the general formula [6]:

$$R_8-SO_3H \qquad [6]$$

(wherein $R^8$ is an alkyl group, an aryl group or an aralkyl group, which may have a halogen atom) or a carboxylic acid shown by the general formula [7]:

$$R^9-COOH \qquad [7]$$

(wherein $R^9$ is an alkyl group, an aryl group or an aralkyl group, which may have a halogen atom).

In the general formulae [8] and [37], the anion derived from the sulfonic acid shown by $A_1$ and $A_4$ includes, for example, one derived from the sulfonic acid shown by the above-mentioned general formula [6].

In the general formula [6], the alkyl group of the alkyl group which may have a halogen atom, shown by $R^8$ may be straight chained, branched or cyclic, and includes one having generally 1 to 29, preferably 1 to 18 and more preferably 1 to 8 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a n-hexadecyl group, an isohexadecyl group, a sec-hexadecyl group, a tert-hexadecyl group, a neohexadecyl group, a n-heptadecyl group, an isoheptadecyl group, a sec-heptadecyl group, a tert-heptadecyl group, a neoheptadecyl group, a n-octadecyl group, an isooctadecyl group, a sec-octadecyl group, a tert-octadecyl group, a neooctadecyl group, a n-nonadecyl group, an isononadecyl group, a sec-nonadecyl group, a tert-nonadecyl group, a neononadecyl group, a n-icosyl group, an isoicosyl group, a sec-icosyl group, a tert-icosyl group, a neoicosyl group, a n-henicosyl group, an isohenicosyl group, a sec-henicosyl group, a tert-henicosyl group, a neohenicosyl group, a n-docosyl group, an isodocosyl group, a sec-docosyl group, a tert-docosyl group, a neodocosyl group, a n-tricosyl group, an isotricosyl group, a sec-tricosyl group, a tert-tricosyl group, a neotricosyl group, a n-tetracosyl group, an isotetracosyl group, a sec-tetracosyl group, a tert-tetracosyl group, a neotetracosyl group, a n-pentacosyl group, an isopentacosyl group, a sec-pentacosyl group, a tert-pentacosyl group, a neopentacosyl group, a n-hexacosyl group, an isohexacosyl group, a sec-hexacosyl group, a tert-hexacosyl group, a neohexacosyl group, a n-heptacosyl group, an isoheptacosyl group, a sec-heptacosyl group, a tert-heptacosyl group, a neoheptacosyl group, a n-octacosyl group, an isooctacosyl group, a sec-octacosyl group, a tert-octacosyl group, a neooctacosyl group, a n-nonacosyl group, an isononacosyl group, a sec-nonacosyl group, a tert-nonacosyl group, a neononacosyl group, a cyclopropyl group, a cyclobutyl group, a cyclopentyl group, a cyclohexyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclohexadecyl group, a cycloheptadecyl group, a cyclooctadecyl group, a cyclononadecyl group, a cycloicosyl group, a cyclohenicosyl group, a cyclodocosyl group, a cyclotricosyl group, a cyclotetracosyl group, a cyclopentacosyl group, a cyclohexacosyl group, a cycloheptacosyl group, a cyclooctacosyl group and a cyclononacosyl group, and among others, for example, a methyl group, a butyl group and an octyl group are preferable.

In the general formula [7], then alkyl group of the alkyl group which may have a halogen atom, shown by $R^9$ may be straight chained, branched or cyclic, and includes one having generally 1 to 29, preferably 1 to 18 and more preferably 1 to 11 carbon atoms, which is specifically exemplified by, for example, the same as examples of the alkyl group of the alkyl group which may have a halogen atom, shown by the above-mentioned $R^8$, and among others, a methyl group, a propyl group, a heptyl group and an undecyl group are preferable.

An aryl group of an aryl group shown by $R^8$ and $R^9$ in the general formulae [6] and [7], which may have a halogen atom, includes one having generally 6 to 16 carbon atoms, preferably 6 to 14 carbon atoms, which is specifically exemplified by, for example, a phenyl group, a naphthyl group, an anthryl group, a phenanthrenyl group and a pyrenyl group, and among others, a phenyl group is preferable.

The aralkyl group of the aralkyl group which may have a halogen atom, shown by $R^8$ and $R^9$ includes one having generally 7 to 15, preferably 7 to 10 carbon atoms, which is specifically exemplified by, for example, a benzyl group, a phenethyl group, a phenylpropyl group, a phenylbutyl group, a 1-methyl-3-phenylpropyl group, a phenylpentyl group, a phenylhexyl group, a phenylheptyl group, a phenyloctyl group and a phenylnonyl group, and among others, a benzyl group and a phenethyl group are preferable.

An alkyl group, an aryl group and an aralkyl group which have a halogen atom, shown by $R^8$ and $R^9$ are one, wherein a part of or all of hydrogen atoms of the above-mentioned alkyl group, aryl group and aralkyl group are substituted by a halogen atom (e.g. a fluorine atom, a chlorine atom, a bromine atom and an iodine atom).

Specifically, in the alkyl group, it is preferable that one, wherein all hydrogen atoms, or generally 1 to 30 hydrogen atoms, preferably 1 to 16 hydrogen atoms thereof are substituted by a halogen atom, and among others, one wherein all hydrogen atoms are substituted by a halogen atom is preferable.

Specifically, in the aryl group, it is preferable that one, wherein 1 to 5 hydrogen atoms, preferably 3 to 5 hydrogen atoms in the ring thereof are substituted by a halogen atom, and among others, one wherein all hydrogen atoms in the ring thereof are substituted by a halogen atom is preferable.

Specifically, in the aralkyl group, it is preferable that one, wherein hydrogen atoms in the alkyl group moiety and/or aryl group moiety are substituted by a halogen atom, and includes one wherein all or a part of hydrogen atoms in the alkyl group moiety thereof are substituted by a halogen atom, and 1 to 5 hydrogen atoms, preferably 5 hydrogen atoms in the aryl ring thereof are substituted by a halogen atom.

An alkyl group, an aryl group or an aralkyl group which may have a halogen atom, shown by $R^8$ and $R^9$, may further have a substituent other than said halogen atom and said substituent includes, for example, a lower alkyl group having 1 to 4 carbon atoms such as a methyl group, an ethyl group, a n-propyl group, an isopropyl group, a n-butyl group, an isobutyl group, a sec-butyl group and a tert-butyl group; a lower haloalkyl group having 1 to 4 carbon atoms such as a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a trifluoroethyl group, a trichloroethyl group, a tribromoethyl group, a pentafluoroethyl group, a pentachloroethyl group, a pentabromoethyl group, a heptafluoropropyl group, a heptachloropropyl group, a nonafluorobutyl group, a nonachlorobutyl group, a nonabromobutyl group and a nonaiodobutyl group; and a lower alkoxy group having 1 to 4 carbon atoms such as a methoxy group, an ethoxy group, a n-propoxy group, an isopropoxy group, a n-butoxy group, an isobutoxy group, a sec-butoxy group and a tert-butoxy group.

The specific example of the compound shown by the general formula [4] includes, for example, tetraphenyl borate, tetrakis[4-(trifluoromethyl)phenyl]borate, tetrakis[4-(trichloromethyl)phenyl]borate, tetrakis[4-(tribromomethyl)phenyl]borate, tetrakis[4-(triiodomethyl)phenyl]borate, tetrakis[3,5-bis(trifluoromethyl)phenyl]borate, tetrakis[3,5-bis(trichloromethyl)phenyl]borate, tetrakis[3,5-bis(tribromomethyl)phenyl]borate, tetrakis[3,5-bis(triiodomethyl)phenyl]borate, tetrakis(pentafluorophenyl)borate, tetrakis(pentachlorophenyl)borate, tetrakis(pentabromophenyl)borate, tetrakis(pentaiodophenyl)borate, tetraphenyl gallate, tetrakis[4-(trifluoromethyl)phenyl]gallate, tetrakis[4-(trichloromethyl)phenyl]gallate, tetrakis[4-(tribromomethyl)phenyl]gallate, tetrakis[4-(triiodomethyl)phenyl]gallate, tetrakis[3,5-bis(trifluoromethyl)phenyl]gallate, tetrakis[3,5-bis(trichloromethyl)phenyl]gallate, tetrakis[3,5-bis(tribromomethyl)phenyl]gallate, tetrakis[3,5-bis(triiodomethyl)phenyl]gallate, tetrakis(pentafluorophenyl)gallate, tetrakis(pentachlorophenyl)gallate, tetrakis(pentabromophenyl)gallate and tetrakis(pentaiodophenyl)gallate, and among others, tetraphenyl borate, tetrakis[4-(trifluoromethyl)phenyl]borate, tetrakis[3,5-bis(trifluoromethyl)phenyl]borate, tetrakis(pentafluorophenyl)borate, tetraphenyl gallate, tetrakis[4-(trifluoromethyl)phenyl]gallate, tetrakis[3,5-bis(trifluoromethyl)phenyl]gallate and tetrakis(pentafluorophenyl)gallate are preferable.

The specific example of the halosulfuric acid as the inorganic strong acid includes, for example, fluorosulfuric acid, chlorosulfuric acid, bromosulfuric acid and iodosulfuric acid, and among others, chlorosulfuric acid and bromosulfuric acid are preferable.

The specific example of the perhalogenic acid as the inorganic strong acid includes, for example, perfluoric acid, perchloric acid, perbromic acid and periodic acid, and among others, a preferable one includes perchloric acid, perbromic acid and periodic acid, and a more preferable one includes perchloric acid.

The specific example of the inorganic strong acid shown by the general formula [5] includes, for example, tetrafluoroborate, tetrafluoroaluminate, tetrafluoroferrate, tetrafluorogallate, hexafluorophosphate, hexafluoroarsenate, hexafluoroantimonate, hexafluorosilicate, hexafluoronickelate, hexafluorotitanate and hexafluorozirconate, and among others, hexafluorophosphate, hexafluoroarsenate and hexafluoroantimonate are preferable.

The specific example of the inorganic strong acid shown by the general formula [36] includes, for example, hexafluorophosphate, hexafluoroarsenate and hexafluoroantimonate.

The specific example of the sulfonic acid shown by the general formula [6] includes, for example, an alkylsulfonic acid such as methanesulfonic acid, ethanesulfonic acid, propanesulfonic acid, butanesulfonic acid, pentanesulfonic acid, hexanesulfonic acid, heptanesulfonic acid, octanesulfonic acid, nonanesulfonic acid, decanesulfonic acid, undecanesulfonic acid, dodecanesulfonic acid, tridecanesulfonic acid, tetradecanesulfonic acid, pentadecanesulfonic acid, hexadecanesulfonic acid, heptadecanesulfonic acid, octadecanesulfonic acid, nonadecanesulfonic acid, icosanesulfonic acid, henicosanesulfonic acid, docosanesulfonic acid, tricosanesulfonic acid and tetracosanesulfonic acid; a haloalkylsulfonic acid such as fluoromethanesulfonic acid, difluoromethanesulfonic acid, trifluoromethanesulfonic acid, chloromethanesulfonic acid, dichloromethanesulfonic acid, trichloromethanesulfonic acid, bromomethanesulfonic acid, dibromomethanesulfonic acid, tribromomethanesulfonic acid, iodomethanesulfonic acid, diiodomethanesulfonic acid, triiodomethanesulfonic acid, fluoroethanesulfonic acid, difluoroethanesulfonic acid, trifluoroethanesulfonic acid, pentafluoroethanesulfonic acid, chloroethanesulfonic acid, dichloroethanesulfonic acid, trichloroethanesulfonic acid, pentachloroethanesulfonic acid, tribromoethanesulfonic acid, pentabromoethanesulfonic acid, triiodoethanesulfonic acid, pentaiodoethanesulfonic acid, fluoropropanesulfonic acid, trifluoropropanesulfonic acid, heptafluoropropanesulfonic acid, chloropropanesulfonic acid, trichloropropanesulfonic acid, heptachloropropanesulfonic acid, bromopropanesulfonic acid, tribromopropanesulfonic acid, heptabromopropanesulfonic acid, triiodopropanesulfonic acid, heptaiodopropanesulfonic acid, trifluorobutanesulfonic acid, nonafluorobutanesulfonic acid, trichlorobutanesulfonic acid, nonachlorobutanesulfonic acid, tribromobutanesulfonic acid, nonabromobutanesulfonic acid, triiodobutanesulfonic acid, nonaiodobutanesulfonic acid, trifluoropentanesulfonic acid, perfluoropentanesulfonic acid, trichloropentanesulfonic acid, perchloropentanesulfonic acid, tribromopentanesulfonic acid, perbromopentanesulfonic acid, triiodopentanesulfonic acid, periodopentanesulfonic acid, trifluorohexanesulfonic acid, perfluorohexanesulfonic acid, trichlorohexanesulfonic acid, perchlorohexanesulfonic acid, perbromohexanesulfonic acid, periodohexanesulfonic acid, trifluoroheptanesulfonic acid, perfluoroheptanesulfonic acid, trichloroheptanesulfonic acid, perchloroheptanesulfonic acid, perbromoheptanesulfonic acid, periodoheptanesulfonic acid, trifluorooctanesulfonic acid, perfluorooctanesulfonic acid, trichlorooctanesulfonic acid, perchlorooctanesulfonic acid, perbromooctanesulfonic acid, periodooctanesulfonic acid, trifluorononanesulfonic acid, perfluorononanesulfonic acid, trichlorononanesulfonic acid, perchlorononanesulfonic acid, perbromononanesulfonic acid, periodononanesulfonic acid, trifluorodecanesulfonic acid, perfluorodecanesulfonic acid, trichlorodecanesulfonic acid, perchlorodecanesulfonic acid, perbromodecanesulfonic acid, periododecanesulfonic acid, trifluoroundecanesulfonic acid, perfluoroundecanesulfonic acid, trichloroundecanesulfonic acid, perchloroundecanesulfonic acid, perbromoundecanesulfonic acid, periodoundecanesulfonic acid, trifluorododecanesulfonic acid, perfluorododecanesulfonic acid, trichlorododecanesulfonic acid, perchlorododecanesulfonic acid, perbromododecanesulfonic acid, periodododecanesulfonic acid, trifluorotridecanesulfonic acid, perfluorotridecanesulfonic acid, trichlorotridecanesulfonic acid, perchlorotridecanesulfonic acid, perbromotridecanesulfonic acid, periodotridecanesulfonic acid, trifluorotetradecanesulfonic acid, perfluorotetradecanesulfonic acid, trichlorotetradecanesulfonic acid, perchlorotetradecanesulfonic acid, perbromotetradecanesulfonic acid, periodotetradecanesulfonic acid, trifluoropentadecanesulfonic acid, perfluoropentadecanesulfonic acid, trichloropentadecanesulfonic acid, perchloropentadecanesulfonic acid, perbromopentadecanesulfonic acid, periodopentadecanesulfonic acid, perfluorohexadecanesulfonic acid, perchlorohexadecanesulfonic acid, perbromohexadecanesulfonic acid, periodohexadecanesulfonic acid, perfluoroheptadecanesulfonic acid, perchloroheptadecanesulfonic acid, perbromoheptadecanesulfonic acid, periodoheptadecanesulfonic acid, perfluorooctadecanesulfonic acid, perchlorooctadecanesulfonic acid, perbromooctadecanesulfonic acid, periodooctadecanesulfonic acid, perfluorononadecanesulfonic acid, perchlorononadecanesulfonic acid, perbromononadecanesulfonic acid, periodononadecanesulfonic acid, perfluoroicosanesulfonic acid, perchloroicosanesulfonic acid, perbromoicosanesulfonic acid, periodoicosanesulfonic acid, perfluorohenicosanesulfonic acid, perchlorohenicosanesulfonic acid, perbromohenicosanesulfonic acid, periodohenicosanesulfonic acid, perfluorodocosanesulfonic acid, perchlorodocosanesulfonic acid, perbromodocosanesulfonic acid, periododocosanesulfonic acid, perfluorotricosanesulfonic acid, perchlorotricosanesulfonic acid, perbromotricosanesulfonic acid, periodotricosanesulfonic acid, perfluorotetracosanesulfonic acid, perchlorotetracosanesulfonic acid, perbromotetracosanesulfonic acid and periodotetracosanesulfonic acid; a cycloalkylsulfonic acid such as cyclopentanesulfonic acid and cyclohexanesulfonic acid; a halocycloalkylsulfonic acid such as 2-fluorocyclopentanesulfonic acid, 2-chlorocyclopentanesulfonic acid, 2-bromocyclopentanesulfonic acid, 2-iodocyclopentanesulfonic acid, 3-fluorocyclopentanesulfonic acid, 3-chlorocyclopentanesulfonic acid, 3-bromocyclopentanesulfonic acid, 3-iodocyclopentanesulfonic acid, 3,4-difluorocyclopentanesulfonic acid, 3,4-dichlorocyclopentanesulfonic acid, 3,4-dibromocyclopentanesulfonic acid, 3,4-diiodocyclopentanesulfonic acid, 4-fluorocyclohexanesulfonic acid, 4-chlorocyclohexanesulfonic acid, 4-bromocyclohexanesulfonic acid, 4-iodocyclohexanesulfonic acid, 2,4-difluorocyclohexanesulfonic acid, 2,4-dichlorocyclohexanesulfonic acid, 2,4-dibromocyclohexanesulfonic acid, 2,4-diiodocyclohexanesulfonic acid, 2,4,6-trifluorocyclohexanesulfonic acid, 2,4,6-trichlorocyclohexanesulfonic acid, 2,4,6-tribromocyclohexanesulfonic acid, 2,4,6-triiodocyclohexanesulfonic acid, tetrafluorocyclohexanesulfonic acid, tetrachlorocyclohexanesulfonic acid, tetrabromocyclohexanesulfonic acid and tetraiodocyclohexanesulfonic acid; an aromatic sulfonic acid such as benzenesulfonic acid, naphthalenesulfonic acid, anthracenesulfonic acid, phenanthrenesulfonic acid and pyrenesulfonic acid; a haloaromatic sulfonic acid such as 2-fluorobenzenesulfonic acid, 3-fluorobenzenesulfonic acid, 4-fluorobenzenesulfonic acid, 2-chlorobenzenesulfonic acid, 3-chlorobenzenesulfonic acid, 4-chlorobenzenesulfonic acid, 2-bromobenzenesulfonic acid, 3-bromobenzenesulfonic acid, 4-bromobenzenesulfonic acid, 2-iodobenzenesulfonic acid, 3-iodobenzenesulfonic acid, 4-iodobenzenesulfonic acid, 2,4-difluorobenzenesulfonic acid, 2,6-difluorobenzenesulfonic acid, 2,4-dichlorobenzenesulfonic acid, 2,6-dichlorobenzenesulfonic acid, 2,4-dibromobenzenesulfonic acid, 2,6-dibromobenzenesulfonic acid, 2,4-diiodobenzenesulfonic acid, 2,6-diiodobenzenesulfonic acid, 2,4,6-trifluorobenzenesulfonic acid, 3,4,5-trifluorobenzenesulfonic acid, 2,4,6-trichlorobenzenesulfonic acid, 3,4,5-trichlorobenzenesulfonic acid, 2,4,6-tribromobenzenesulfonic acid, 3,4,5-tribromobenzenesulfonic acid, 2,4,6-triiodobenzenesulfonic acid, 3,4,5-triiodobenzenesulfonic acid, pentafluorobenzenesulfonic acid, pentachlorobenzenesulfonic acid, pentabromobenzenesulfonic acid, pentaiodobenzenesulfonic acid, fluoronaphthalenesulfonic acid, chloronaphthalenesulfonic acid, bromonaphthalenesulfonic acid, iodonaphthalenesulfonic acid, fluoroanthracenesulfonic acid, chloroanthracenesulfonic acid, bromoanthracenesulfonic acid and iodoanthracenesulfonic acid; an alkylaromatic sulfonic acid such as p-toluenesulfonic acid, 4-isopropylbenzenesulfonic acid, 3,5-bis(trimethyl)benzenesulfonic acid, 3,5-bis(isopropyl)benzenesulfonic acid, 2,4,6-tris(trimethyl)benzenesulfonic acid and 2,4,6-tris(isopropyl)benzenesulfonic acid; a haloalkylaromatic sulfonic acid such as 2-trifluoromethylbenzenesulfonic acid, 2-trichloromethylbenzenesulfonic acid, 2-tribromomethylbenzenesulfonic acid, 2-triiodomethylbenzenesulfonic acid, 3-trifluoromethylbenzenesulfonic acid, 3-trichloromethylbenzenesulfonic acid, 3-tribromomethylbenzenesulfonic acid, 3-triiodomethylbenzenesulfonic acid, 4-trifluoromethylbenzenesulfonic acid, 4-trichloromethylbenzenesulfonic acid, 4-tribromomethylbenzenesulfonic acid, 4-triiodomethylbenzenesulfonic acid, 2,6-bis(trifluoromethyl)benzenesulfonic acid, 2,6-bis(trichloromethyl)benzenesulfonic acid, 2,6-bis(tribromomethyl)benzenesulfonic acid, 2,6-bis(triiodomethyl)benzenesulfonic acid, 3,5-bis(trifluoromethyl)benzenesulfonic acid, 3,5-bis(trichloromethyl)benzenesulfonic acid, 3,5-bis(tribromomethyl)benzenesulfonic acid and 3,5-bis(triiodomethyl)benzenesulfonic acid; an aromatic aliphatic sulfonic acid such as benzylsulfonic acid, phenethylsulfonic acid, phenylpropylsulfonic acid, phenylbutylsulfonic acid, phenylpentylsulfonic acid, phenylhexylsulfonic acid, phenylheptylsulfonic acid, phenyloctylsulfonic acid and phenylnonylsulfonic acid; a haloaromatic aliphatic sulfonic acid such as 4-fluorophenylmethylsulfonic acid, 4-chlorophenylmethylsulfonic acid, 4-bromophenylmethylsulfonic acid, 4-iodophenylmethylsulfonic acid, tetrafluorophenylmethylsulfonic acid, tetrachlorophenylmethylsulfonic acid, tetrabromophenylmethylsulfonic acid, tetraiodophenylmethylsulfonic acid, 4-fluorophenylethylsulfonic acid, 4-chlorophenylethylsulfonic acid, 4-bromophenylethylsulfonic acid, 4-iodophenylethylsulfonic acid, 4-fluorophenylpropylsulfonic acid, 4-chlorophenylpropylsulfonic acid, 4-bromophenylpropylsulfonic acid, 4-iodophenylpropylsulfonic acid, 4-fluorophenylbutylsulfonic acid, 4-chlorophenylbutylsulfonic acid, 4-bromophenylbutylsulfonic acid and 4-iodophenylbutylsulfonic acid; and an alicyclic sulfonic acid such as camphorsulfonic acid and adamantanesulfonic acid.

The specific example of the carboxylic acid shown by the general formula [7] includes, for example, a saturated aliphatic carboxylic acid such as formic acid, acetic acid, propionic acid, butyric acid, isobutyric acid, valeric acid, isovaleric acid, pivalic acid, hexanoic acid, peptanoic acid, octanoic acid, nonanoic acid, decanoic acid, undecanoic acid, lauric acid, tridecanoic acid, myristic acid, pentadecanoic acid, palmitic acid, heptadecanoic acid, stearic acid, nonadecanoic acid, icosanoic acid, henicosanoic acid, docosanoic acid and tricosanoic acid; a saturated haloaliphatic carboxylic acid such as fluoroacetic acid, chloroacetic acid, bromoacetic acid, iodoacetic acid, difluoroacetic acid, dichloroacetic acid, dibromoacetic acid, diiodoacetic acid, trifluroacetic acid, trichloroacetic acid, tribromoacetic acid, triiodmoacetic acid, 2-fluoropropionic acid, 2-chloropropionic acid, 2-bromopropionic acid, 2-iodopropionic acid, trifluoropropionic acid, trichloropropionic acid, pentafluoropropionic acid, pentachloropropionic acid, pentabromopropionic acid, pentaiodopropionic acid, 2,2-bis (trifluoromethyl)propionic acid, 2,2-bis(trichloromethyl) propionic acid, 2,2-bis(tribromomethyl)propionic acid, 2,2-bis(triiodomethyl)propionic acid, trifluorobutyric acid, trichlorobutyric acid, pentafluorobutyric acid, heptachlorobutyric acid, heptafluorobutyric acid, heptabromobutyric acid, heptaiodobutyric acid, heptafluoroisobutyric acid, heptachloroisobutyric acid, heptabromoisobutyric acid, heptaiodoisobutyric acid, trifluorovaleric acid, 5H-perfluorovaleric acid, 5H-perchlorovaleric acid, 5H-perbromovaleric acid, 5H-periodovaleric acid, nonafluorovaleric acid, nonachlorovaleric acid, nonabromovaleric acid, nonaiodovaleric acid, trifluorohexanoic acid, trichlorohexanoic acid, perfluorohexanoic acid, perchlorohexanoic acid, perbromohexanoic acid, periodohexanoic acid, 7-chlorododecafluoroheptanoic acid, 7-chlorododecachloroheptanoic acid, 7-chlorododecabromoheptanoic acid, 7-chlorododecaiodoheptanoic acid, trifluoroheptanoic acid, trichloroheptanoic acid, 7H-perfluoroheptanoic acid, 7H-perchloroheptanoic acid, 7H-perbromoheptanoic acid, 7H-periodoheptanoic acid, trifluorooctanoic acid, trichlorooctanoic acid, pentadecafluorooctanoic acid, pentadecachlorooctanoic acid, pentadecabromooctanoic acid, pentadecaiodooctanoic acid, trifluorononanoic acid, trichlorononanoic acid, 9H-hexadecafluorononanoic acid, 9H-hexadecachlorononanoic acid, 9H-hexadecabromononanoic acid, 9H-hexadecaiodononanoic acid, perfluorononanoic acid, perchlorononanoic acid, perbromononanoic acid, periodononanoic acid, trifluorodecanoic acid, trichlorodecanoic acid, nonadecafluorodecanoic acid, nonadecachlorodecanoic acid, nonadecabromodecanoic acid, nonadecaiodododecanoic acid, trifluoroundecanoic acid, trichloroundecanoic acid, perfluoroundecanoic acid, perchloroundecanoic acid, perbromoundecanoic acid, periodoundecanoic acid, trifluorododecanoic acid, trichlorododecanoic acid, perfluorododecanoic acid, perchlorododecanoic acid, perbromododecanoic acid, periodododecanoic acid, trifluorotridecanoic acid, trichlorotridecanoic acid, perfluorotridecanoic acid, perchlorotridecanoic acid, perbromotridecanoic acid, periodotridecanoic acid, trifluorotetradecanoic acid, trichlorotetradecanoic acid, perfluorotetradecanoic acid, perchlorotetradecanoic acid, perbromotetradecanoic acid, periodotetradecanoic acid, trifluoropentadecanoic acid, trichloropentadecanoic acid, perfluoropentadecanoic acid, perchloropentadecanoic acid, perbromopentadecanoic acid, periodopentadecanoic acid, perfluorohexadecanoic acid, perchlorohexadecanoic acid, perbromohexadecanoic acid, periodohexadecanoic acid, perfluoroheptadecanoic acid, perchloroheptadecanoic acid, perbromoheptadecanoic acid, periodoheptadecanoic acid, perfluorooctadecanoic acid, perchlorooctadecanoic acid, perbromooctadecanoic acid, periodooctadecanoic acid, perfluorononadecanoic acid, perchlorononadecanoic acid, perbromononadecanoic acid, periodononadecanoic acid, perfluoroicosanoic acid, perchloroicosanoic acid, perbromoicosanoic acid, periodoicosanoic acid, perfluorohenicosanoic acid, perchlorohenicosanoic acid, perbromohenicosanoic acid, periodohenicosanoic acid, perfluorodocosanoic acid, perchlorodocosanoic acid, perbromodocosanoic acid, periododocosanoic acid, perfluorotricosanoic acid, perchlorotricosanoic acid, perbromotricosanoic acid and periodotricosanoic acid; a hydroxyaliphatic carboxylic acid such as glycolic acid, lactic acid, glyceric acid and 3-hydroxy-2-methylpropionic acid; a hydroxyhaloaliphatic carboxylic acid such as 3-hydroxy-2-(trifluoromethyl)propionic acid, 3-hydroxy-2-(trichloromethyl)propionic acid, 3-hydroxy-2-(tribromomethyl)propionic acid, 3-hydroxy-2-(triiodomethyl)propionic acid, 2-hydroxy-2-(trifluoromethyl)butyric acid, 2-hydroxy-2-(trichloromethyl)butyric acid, 2-hydroxy-2-(tribromomethyl)butyric acid and 2-hydroxy-2-(triiodomethyl)butyric acid; an alicyclic carboxylic acid such as cyclohexanecarboxylic acid, camphoric acid and adamantane carboxylic acid; a haloalicyclic carboxylic acid such as 4-fluorocyclohexanecarboxylic acid, 4-chlorocyclohexanecarboxylic acid, 4-bromocyclohexanecarboxylic acid, 4-iodocyclohexanecarboxylic acid, pentafluorocyclohexanecarboxylic acid, pentachlorocyclohexanecarboxylic acid, pentabromocyclohexanecarboxylic acid, pentaiodocyclohexanecarboxylic acid, 4-(trifluoromethyl)cyclohexanecarboxylic acid, 4-(trichloromethyl)cyclohexanecarboxylic acid, 4-(tribromomethyl)cyclohexanecarboxylic acid and 4-(triiodomethyl)cyclohexanecarboxylic acid; an aromatic carboxylic acid such as benzoic acid, naphthoic acid, anthracene carboxylic acid, pyrene carboxylic acid, perylene carboxylic acid and pentaphene carboxylic acid; a haloaromatic carboxylic acid such as fluorobenzoic acid, chlorobenzoic acid, bromobenzoic acid, iodobenzoic acid, difluorobenzoic acid, dichlorobenzoic acid, dibromobenzoic acid, diiodobenzoic acid, trifluorobenzoic acid, trichlorobenzoic acid, tribromobenzoic acid, triiodobenzoic acid, tetrafluorobenzoic acid, tetrachlorobenzoic acid, tetrabromobenzoic acid, tetraiodobenzoic acid, pentafluorobenzoic acid, pentachlorobenzoic acid, pentabromobenzoic acid, pentaiodobenzoic acid, fluoronaphthoic acid, chloronaphthoic acid, bromonaphthoic acid, iodonaphthoic acid, perfluoronaphthoic acid, perchloronaphthoic acid, perbromonaphthoic acid, periodonaphthoic acid, fluoroanthracene carboxylic acid, chloroanthracene carboxylic acid, bromoanthracene carboxylic acid, iodoanthracene carboxylic acid, perfluoroanthracene carboxylic acid, perchloroanthracene carboxylic acid, perbromoanthracene carboxylic acid and periodoanthracene carboxylic acid; an alkylaromatic carboxylic acid such as toluic acid and 2,4,6-tri(isopropyl)benzoic acid; a haloalkylaromatic carboxylic acid such as 2-trifluoromethylbenzoic acid, 2-trichloromethylbenzoic acid, 2-tribromomethylbenzoic acid, 2-triiodomethylbenzoic acid, 3-trifluoromethylbenzoic acid, 3-trichloromethylbenzoic acid, 3-tribromomethylbenzoic acid, 3-triiodomethylbenzoic acid, 4-trifluoromethylbenzoic acid, 4-trichloromethylbenzoic acid, 4-tribromomethylbenzoic acid, 4-triiodomethylbenzoic acid, 2-fluoro-4-(trifluoromethyl)benzoic acid, 2-chloro-4-(trichloromethyl)benzoic acid, 2-bromo-4-(tribromomethyl)benzoic acid, 2,3,4-trifluoro-6-(trifluoromethyl)benzoic acid, 2,3,4-trichloro-6-(trichloromethyl)benzoic acid, 2,3,4-tribromo-6-(tribromomethyl)benzoic acid, 2,3,4-triiodo-6-(triiodomethyl)benzoic acid, 2-iodo-4-(triiodomethyl)benzoic acid, 2,4-bis(trifluoromethyl)benzoic acid, 2,4-bis(trichloromethyl)benzoic acid, 2,4-bis(tribromomethyl)benzoic acid, 2,4-bis(triiodomethyl)benzoic acid, 2,6-bis(trifluoromethyl)benzoic acid, 2,6-bis(trichloromethyl)benzoic acid, 2,6-bis(tribromomethyl)benzoic acid, 2,6-bis(triiodomethyl)benzoic acid, 3,5-bis(trifluoromethyl)benzoic acid, 3,5-bis(trichloromethyl)benzoic acid, 3,5-bis(tribromomethyl)benzoic acid, 3,5-bis(triiodomethyl)benzoic acid, 2,4,6-tris(trifluoromethyl)benzoic acid, 2,4,6-tris(trichloromethyl)benzoic acid, 2,4,6-tris(tribromomethyl)benzoic acid, 2,4,6-tris(triiodomethyl)benzoic acid, 2-chloro-6-fluoro-3-methylbenzoic acid, trifluoromethylnaphthoic acid, trichloromethylnaphthoic acid, tribromomethylnaphthoic acid, triiodomethylnaphthoic acid, bis(trifluoromethyl)naphthoic acid, bis(trichloromethyl)naphthoic acid, bis(tribromomethyl)naphthoic acid, bis(triiodomethyl)naphthoic acid, tris(trifluoromethyl)naphthoic acid, tris(trichloromethyl)naphthoic acid, tris(tribromomethyl)naphthoic acid, tris(triiodomethyl)naphthoic acid, trifluoromethylanthracene carboxylic acid, trichloromethylanthracene carboxylic acid, tribromomethylanthracene carboxylic acid and triiodomethylanthracene carboxylic acid; an alkoxyaromatic carboxylic acid such as anisic acid, veratric acid and o-veratric acid; a haloalkoxyaromatic carboxylic acid such as 4-trifluoromethoxybenzoic acid, 4-trichloromethoxybenzoic acid, 4-tribromomethoxybenzoic acid, 4-triiodomethoxybenzoic acid, 4-pentafluoroethoxybenzoic acid, 4-pentachloroethoxybenzoic acid, 4-pentabromoethoxybenzoic acid, 4-pentaiodoethoxybenzoic acid, 3,4-bis(trifluoromethoxy)benzoic acid, 3,4-bis(trichloromethoxy)benzoic acid, 3,4-bis(tribromomethoxy)benzoic acid, 3,4-bis(triiodomethoxy)benzoic acid, 2,5-bis(2,2,2-trifluoroethoxy)benzoic acid, 2,5-bis(2,2,2-trichloroethoxy)benzoic acid, 2,5-bis(2,2,2-tribromoethoxy)benzoic acid and 2,5-bis(2,2,2-triiodoethoxy)benzoic acid; a hydroxyaromatic carboxylic acid such as salicylic acid, o-pyrocatechuic acid, β-resorcylic acid, gentisic acid, γ-resorcylic acid, protocatechuic acid, α-resorcylic acid and gallic acid; a hydroxyalkoxyaromatic carboxylic acid such as vanillic acid and isovanillic acid; a nitroaromatic carboxylic acid such as trinitrobenzoic acid; an amino aromatic carboxylic acid such as anthranilic acid; an aromaticaliphatic carboxylic acid such as α-toluic acid, hydrocinnamic acid, hydroatropic acid, 3-phenylpropionic acid, 4-phenylbutyric acid, 5-phenylpentanoic acid, 6-phenylhexanoic acid, 7-phenylheptanoic acid and 6-(2-naphthyl)hexanoic acid; a hydroxyaromaticaliphatic carboxylic acid such as homogentisic acid; an aromatic hydroxyalkyl carboxylic acid such as mandelic acid, benzylic acid, atrolactinic acid, tropic acid and atroglyceric acid; an oxocarboxylic acid such as 2-formylacetic acid, acetoacetic acid, 3-benzoylpropionic acid, 4-formylacetic acid, 3-oxovaleric acid, 3,5-dioxovaleric acid, 6-formylhexanecarboxylic acid, 2-oxo-1-cyclohexanecarboxylic acid, 4-(2-oxobutyl)benzoic acid, p-(3-formylpropyl)benzoic acid, 4-formylphenylacetic acid, β-oxocyclohexanepropionic acid and pyruvic acid.

The group shown by the general formula [2] includes, for example, a group shown by the following general formula [10] and [12]:

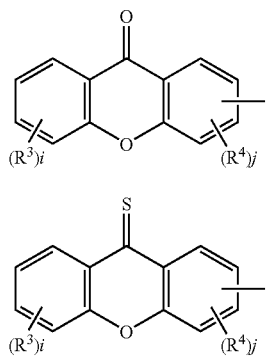

(wherein $R^3$, $R^4$, i and j have the same meaning as above), and among others, a group shown by the general formula [10] is preferable.

The group shown by the general formula [10] includes, for example, a xanthene-9-one-2-yl group and a xanthene-9-one-4-yl group, and among others, a xanthene-9-one-2-yl group is preferable.

The group shown by the general formula [3] includes, for example, a group shown by the following general formula [14] and [15]:

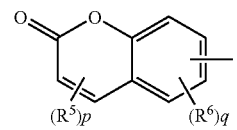

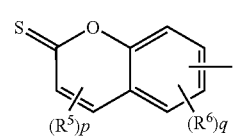

(wherein $R^5$, $R^6$, p and q have the same meaning as above), and among others, a group shown by the general formula [14] is preferable.

The group shown by the general formula [14] includes, for example, a coumarin-7-yl group, a coumarin-5-yl group, a 4-methoxycoumarin-7-yl group, a 4-methoxycoumarin-5-yl group, 6-methylcoumarin-7-yl group and a 6-methylcoumarin-5-yl group, and among others, a coumarin-7-yl group is preferable.

The group shown by the general formula [15] includes, for example, a coumarin-2-thione-7-yl group, a coumarin-2-thione-5-yl group, a 4-methoxycoumarin-2-thione-7-yl group, a 4-methoxycoumarin-2-thione-5-yl group, 6-methylcoumarin-2-thione-7-yl group and a 6-methylcoumarin-2-thione-5-yl group.

The sulfonium salt shown by the general formula [1] includes, for example, a group shown by the following general formulae [16], [18], [20] and [21]:

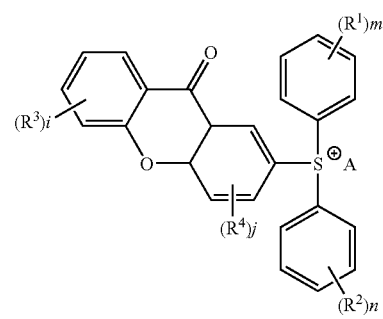

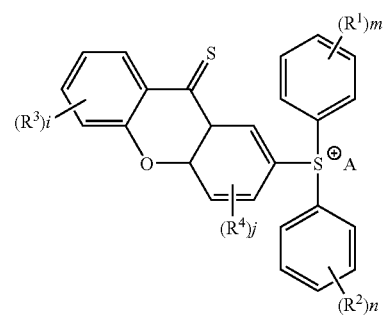

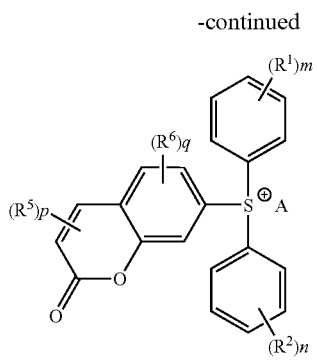
[20]

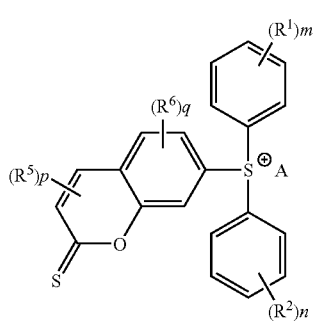
[21]

(wherein R[1] to R[6], A, i, j, m, n, p and q have the same meaning as above), and among others, groups shown by the general formulae [16] and [20] are preferable.

The iodonium salt shown by the general formula [35] includes, for example, one shown by the following general formulae [39] to [43]:

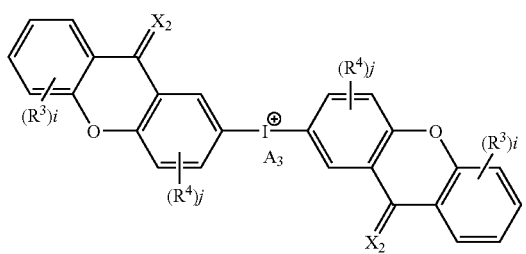
[39]

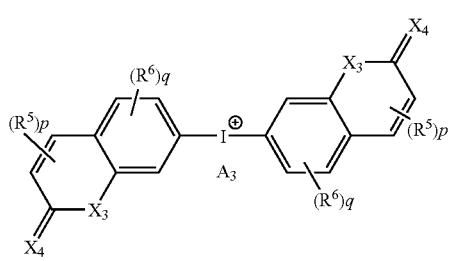
[40]

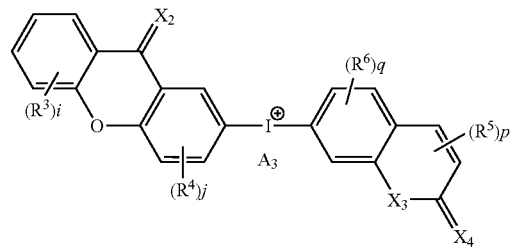
[41]

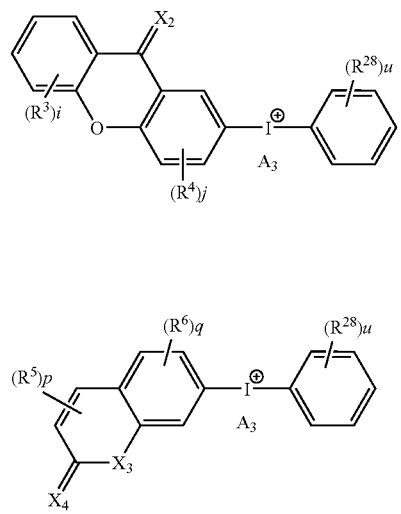
[42]

[43]

(wherein $R^{28}$ is a halogen atom or a lower alkyl group; u is an integer of 0 to 5; and $R^1$ to $R^6$, $X_2$ to $X_4$, $A_3$, i, j, m, n, p and q have the same meaning as above), and among others, groups shown by the general formulae [39] to [41] are preferable, and groups shown by the general formulae [39] and [40] are more preferable.

In the general formulae [42] and [43], the halogen atom shown by $R^{28}$ includes, for example, a fluorine atom, a chlorine atom, a bromine atom and an iodine atom.

The lower alkyl group shown by $R^{28}$ may be straight chained, branched or cyclic, and includes one having generally 1 to 6, preferably 1 to 4 carbon atoms, which is specifically exemplified by, for example, the lower alkyl group examples as the substituent of an aryl group which may have a halogen atom or a lower alkyl group as a substituent, shown by the above $R^1$ to $R^6$ and among others, a preferable one includes, for example, a methyl group, an ethyl group, a n-propyl group, an isopropyl group, a n-butyl group, an isobutyl group, a sec-butyl group and a tert-butyl group, and a more preferable one includes a methyl group and an ethyl group.

U is an integer of generally 0 to 5, preferably 0 to 1.

The preferable specific example shown by the general formula [16] includes, for example, diphenyl(xanthene-9-one-2-yl)sulfonium chloride, diphenyl(xanthene-9-one-2-yl)sulfonium bromide, diphenyl(xanthene-9-one-2-yl)sulfonium perchlorate, diphenyl(xanthene-9-one-2-yl)sulfonium tetrafluoroborate, diphenyl(xanthene-9-one-2-yl)sulfonium hexafluorophosphate, diphenyl(xanthene-9-one-2-yl)sulfonium hexafluoroarsenate, diphenyl(xanthene-9-one-2-yl)sulfonium hexafluoroantimonate, diphenyl(xanthene-9-one-2-yl)sulfonium tetraphenylborate, diphenyl(xanthene-9-one-2-yl)sulfonium tetrakis{3,5-bis(trifluoromethyl)phenyl}borate, diphenyl(xanthene-9-one-2-yl)sulfonium tetrakis(pentafluorophenyl)borate, diphenyl(xanthene-9-one-2-yl)sulfonium tetraphenylgallate, diphenyl(xanthene-9-one-2-yl)sulfonium tetrakis(pentafluorophenyl)gallate, diphenyl(xanthene-9-one-2-yl)sulfonium trifluoromethanesulfonate, diphenyl(xanthene-9-one-2-yl)sulfonium nonafluorobutanesulfonate, diphenyl(xanthene-9-one-2-yl)sulfonium perfluorooctanesulfonate, diphenyl(xanthene-9-one-2-yl)sulfonium benzenesulfonate, diphenyl(xanthene-9-one-2-yl)sulfonium p-toluenesulfonate, diphenyl(xanthene-9-one-2-yl)sulfonium 4-dodecylbenzenesulfonate, diphenyl(xanthene-9-one-2-yl)sulfonium 4-fluorobenzenesulfonate, diphenyl(xanthene-9-one-2-yl)sulfonium, 2,4-difluorobenzenesulfonate, diphenyl(xanthene-9-one-2-yl)sulfonium pentafluorobenzenesulfonate, diphenyl(xanthene-9-one-2-yl)sulfonium 4-trifluoromethylbenzenesulfonate, diphenyl(xanthene-9-one-2-yl)sulfonium 3,5-bis(trifluoromethyl)benzenesulfonate, diphenyl(xanthene-9-one-2-yl)sulfonium acetate, diphenyl(xanthene-9-one-2-yl)sulfonium heptafluorobutanoate, diphenyl(xanthene-9-one-2-yl)sulfonium perfluorooctanoate, diphenyl(xanthene-9-one-2-yl)sulfonium perfluorododecanoate, bis(4-methylphenyl)(xanthene-9-one-2-yl)sulfonium hexafluorophosphate, bis(4-methylphenyl)(xanthene-9-one-2-yl)sulfonium tetraphenylborate, bis(4-methylphenyl)(xanthene-9-one-2-yl)sulfonium trifluoromethanesulfonate, bis(4-methylphenyl)(xanthene-9-one-2-yl)sulfonium nonafluorobutanesulfonate, bis(4-methylphenyl)(xanthene-9-one-2-yl)sulfonium p-toluenesulfonate, diphenyl(xanthene-9-one-4-yl)sulfonium hexafluorophosphate, diphenyl(xanthene-9-one-4-yl)sulfonium tetraphenylborate, diphenyl(xanthene-9-one-4-yl)sulfonium trifluoromethanesulfonate, diphenyl(xanthene-9-one-4-yl)sulfonium nonafluorobutanesulfonate and diphenyl(xanthene-9-one-4-yl)sulfonium p-toluenesulfonate, and among others, a preferable one includes, for example, diphenyl(xanthene-9-one-2-yl)sulfonium hexafluorophosphate, diphenyl(xanthene-9-one-2-yl)sulfonium tetrafluoroborate, diphenyl(xanthene-9-one-2-yl)sulfonium trifluoromethanesulfonate, diphenyl(xanthene-9-one-2-yl)sulfonium nonafluorobutanesulfonate and diphenyl(xanthene-9-one-2-yl)sulfonium p-toluenesulfonate, among others, a more preferable includes diphenyl(xanthene-9-one-2-yl)sulfonium trifluoromethanesulfonate and diphenyl(xanthene-9-one-2-yl)sulfonium hexafluorophosphate.

The preferable specific example shown by the general formula [18] includes, for example, diphenyl(xanthene-9-thione-2-yl)sulfonium chloride, diphenyl(xanthene-9-thione-2-yl)sulfonium bromide, diphenyl(xanthene-9-thione-2-yl)sulfonium perchlorate, diphenyl(xanthene-9-thione-2-yl)sulfonium tetrafluoroborate, diphenyl(xanthene-9-thione-2-yl)sulfonium hexafluorophosphate, diphenyl(xanthene-9-thione-2-yl)sulfonium hexafluoroarsenate, diphenyl(xanthene-9-thione-2-yl)sulfonium hexafluoroantimonate, diphenyl(xanthene-9-thione-2-yl)sulfonium tetraphenylborate, diphenyl(xanthene-9-thione-2-yl)sulfonium tetrakis{3,5-bis(trifluoromethyl)phenyl}borate, diphenyl(xanthene-9-thione-2-yl)sulfonium, tetrakis(pentafluorophenyl)borate, diphenyl(xanthene-9-thione-2-yl)sulfonium tetraphenylgallate, diphenyl(xanthene-9-thione-2-yl)sulfonium trifluoromethanesulfonate, diphenyl(xanthene-9-thione-2-yl)sulfonium nonafluorobutanesulfonate, diphenyl(xanthene-9-thione-2-yl)sulfonium perfluorooctanesulfonate, diphenyl(xanthene-9-thione-2-yl)sulfonium benzenesulfonate, diphenyl(xanthene-9-thione-2-yl)sulfonium p-toluenesulfonate, diphenyl(xanthene-9-thione-2-yl)sulfonium acetate, diphenyl(xanthene-9-thione-2-yl)sulfonium heptafluorobutanoate, diphenyl(xanthene-9-thione-2-yl)sulfonium perfluorooctanoate, bis(4-methylphenyl)(xanthene-9-thione-2-yl)sulfonium hexafluorophosphate, bis(4-methylphenyl)(xanthene-9-thione-2-yl)sulfonium tetraphenylborate, bis(4-methylphenyl) (xanthene-9-thione-2-yl)sulfonium trifluoromethanesulfonate, bis(4-methylphenyl)(xanthene-9-thione-2-yl)sulfonium nonafluorobutanesulfonate, bis(4-methylphenyl)(xanthene-9-thione-2-yl)sulfonium p-toluenesulfonate, diphenyl(xanthene-9-thione-4-yl)sulfonium hexafluorophosphate, diphenyl(xanthene-9-thione-4-yl)sulfonium tetraphenylborate, diphenyl(xanthene-9-thione-4-yl)sulfonium trifluoromethanesulfonate, diphenyl(xanthene-9-thione-4-yl)sulfonium nonafluorobutanesulfonate and diphenyl(xanthene-9-thione-4-yl)sulfonium p-toluenesulfonate, and among others, a preferable one includes, for example, diphenyl(xanthene-9-thione-2-yl)sulfonium hexafluorophosphate, diphenyl(xanthene-9-thione-2-yl)sulfonium tetraphenylborate, diphenyl(xanthene-9-thione-2-yl)sulfonium trifluoromethanesulfonate, diphenyl(xanthene-9-thione-2-yl)sulfonium nonafluorobutanesulfonate and diphenyl(xanthene-9-thione-2-yl)sulfonium p-toluenesulfonate.

The preferable specific example shown by the general formula [20] includes, for example, diphenyl(coumarin-7-yl)sulfonium chloride, diphenyl(coumarin-7-yl)sulfonium bromide, diphenyl(coumarin-7-yl)sulfonium perchlorate, diphenyl(coumarin-7-yl)sulfonium tetrafluoroborate, diphenyl(coumarin-7-yl)sulfonium hexafluorophosphate, diphenyl(coumarin-7-yl)sulfonium hexafluoroarsenate, diphenyl(coumarin-7-yl)sulfonium hexafluoroantimonate, diphenyl(coumarin-7-yl)sulfonium tetraphenylborate, diphenyl(coumarin-7-yl)sulfonium tetrakis{3,5-bis(trifluoromethyl)phenyl}borate, diphenyl(coumarin-7-yl)sulfonium tetrakis(pentafluorophenyl)borate, diphenyl(coumarin-7-yl)sulfonium tetrafluorogallate, diphenyl(coumarin-7-yl)sulfonium tetraphenylgallate, diphenyl(coumarin-7-yl)sulfonium tetrakis(pentafluorophenyl)gallate, diphenyl(coumarin-7-yl)sulfonium trifluoromethanesulfonate, diphenyl(coumarin-7-yl)sulfonium nonafluorobutanesulfonate, diphenyl(coumarin-7-yl)sulfonium perfluorooctanesulfonate, diphenyl(coumarin-7-yl)sulfonium benzenesulfonate, diphenyl(coumarin-7-yl)sulfonium p-toluenesulfonate, diphenyl(coumarin-7-yl)sulfonium 4-dodecylbenzenesulfonate, diphenyl(coumarin-7-yl)sulfonium 4-fluorobenzenesulfonate, diphenyl(coumarin-7-yl)sulfonium 2,4-difluorobenzenesulfonate, diphenyl(coumarin-7-yl)sulfonium pentafluorobenzenesulfonate, diphenyl(coumarin-7-yl)sulfonium 4-trifluoromethylbenzenesulfonate, diphenyl(coumarin-7-yl)sulfonium 3,5-bis(trifluoromethyl)benzenesulfonate, diphenyl(coumarin-7-yl)sulfonium acetate, diphenyl(coumarin-7-yl)sulfonium heptafluorobutanoate, diphenyl(coumarin-7-yl)sulfonium perfluorooctanoate, diphenyl(coumarin-7-yl)sulfonium perfluorododecanoate, bis(4-methylphenyl)(coumarin-7-yl)sulfonium hexafluorophosphate, bis(4-methylphenyl) (coumarin-7-yl)sulfonium tetraphenylborate, bis(4-methylphenyl) (coumarin-7-yl)sulfonium trifluoromethanesulfonate, bis(4-methylphenyl)(coumarin-7-yl)sulfonium nonafluorobutanesulfonate, bis(4-methylphenyl)(coumarin-7-yl)sulfonium p-toluenesulfonate, diphenyl(4-methoxycoumarin-7-yl)sulfonium hexafluorophosphate, diphenyl(4-methoxycoumarin-7-yl)sulfonium tetraphenylborate, diphenyl(4-methoxycoumarin-7-yl)sulfonium trifluoromethanesulfonate, diphenyl(4-methoxycoumarin-7-yl)sulfonium nonafluorobutanesulfonate, diphenyl(4-methoxycoumarin-7-yl)sulfonium p-toluenesulfonate, diphenyl(6-methylcoumarin-7-yl)sulfonium hexafluorophosphate, diphenyl(6-methylcoumarin-7-yl)sulfonium tetraphenylborate, diphenyl(6-methylcoumarin-7-yl)sulfonium trifluoromethanesulfonate, diphenyl(6-methylcoumarin-7-yl)sulfonium nonafluorobutanesulfonate, diphenyl(6-methylcoumarin-7-yl)sulfonium p-toluenesulfonate, diphenyl(coumarin-5-yl)sulfonium hexafluorophosphate, diphenyl(coumarin-5-yl)sulfonium tetraphenylborate, diphenyl(coumarin-5-yl)sulfonium trifluoromethanesulfonate, diphenyl(coumarin-5-yl)sulfonium nonafluorobutanesulfonate and diphenyl(coumarin-5-yl)sulfonium p-toluenesulfonate, and among others, a preferable one incdlues diphenyl(coumarin-7-yl)sulfonium hexafluorophosphate, diphenyl(coumarin-7-yl)sulfonium tetraphenylborate, diphenyl(coumarin-7-yl)sulfonium trifluoromethanesulfonate, diphenyl(coumarin-7-yl)sulfonium nonafluorobutanesulfonate and diphenyl(coumarin-7-yl)sulfonium p-toluenesulfonate, a more preferable includes diphenyl(coumarin-7-yl)sulfonium trifluoromethanesulfonate and diphenyl(coumarin-7-yl)sulfonium hexafluorophosphate.

The preferable specific example shown by the general formula [21] includes, for example, diphenyl(coumarin-2-thione-7-yl)sulfonium chloride, diphenyl(coumarin-2-thione-7-yl)sulfonium bromide, diphenyl(coumarin-2-thione-7-yl)sulfonium perchlorate, diphenyl(coumarin-2-thione-7-yl)sulfonium tetrafluoroborate, diphenyl(coumarin-2-thione-7-yl)sulfonium hexafluorophosphate, diphenyl(coumarin-2-thione-7-yl)sulfonium hexafluoroarsenate, diphenyl(coumarin-2-thione-7-yl)sulfonium hexafluoroantimonate, diphenyl(coumarin-2-thione-7-yl)sulfonium tetraphenylborate, diphenyl(coumarin-2-thione-7-yl)sulfonium tetrakis{3,5-bis(trifluoromethyl)phenyl}borate, diphenyl(coumarin-2-thione-7-yl)sulfonium tetrakis(pentafluorophenyl)borate, diphenyl(coumarin-2-thione-7-yl)sulfonium tetrafluorogallate, diphenyl(coumarin-2-thione-7-yl)sulfonium trifluoromethanesulfonate, diphenyl(coumarin-2-thione-7-yl)sulfonium nonafluorobutanesulfonate, diphenyl(coumarin-2-thione-7-yl)sulfonium perfluorooctanesulfonate, diphenyl(coumarin-2-thione-7-yl)sulfonium benzenesulfonate, diphenyl(coumarin-2-thione-7-yl)sulfonium p-toluenesulfonate, diphenyl(coumarin-2-thione-7-yl)sulfonium acetate, diphenyl(coumarin-2-thione-7-yl)sulfonium heptafluorobutanoate, diphenyl(coumarin-2-thione-7-yl)sulfonium perfluorooctanoate, bis(4-methylphenyl)(coumarin-2-thione-7-yl)sulfonium hexafluorophosphate, bis(4-methylphenyl)(coumarin-2-thione-7-yl)sulfonium tetraphenylborate, bis(4-methylphenyl)(coumarin-2-thione-7-yl)sulfonium trifluoromethanesulfonate, bis(4-methylphenyl)(coumarin-2-thione-7-yl)sulfonium nonafluorobutanesulfonate, bis(4-methylphenyl)(coumarin-2-thione-7-yl)sulfonium p-toluenesulfonate, diphenyl(coumarin-2-thione-5-yl)sulfonium hexafluorophosphate, diphenyl(coumarin-2-thione-5-yl)sulfonium tetraphenylborate, diphenyl(coumarin-2-thione-5-yl)sulfonium trifluoromethanesulfonate, diphenyl(coumarin-2-thione-5-yl)sulfonium nonafluorobutanesulfonate and diphenyl(coumarin-2-thione-5-yl)sulfonium p-toluenesulfonate, and among others, a preferable one includes, for example, diphenyl(coumarin-2-thione-7-yl)sulfonium hexafluorophosphate, diphenyl coumarin-2-thione-7-yl)sulfonium tetraphenylborate, diphenyl(coumarin-2-thione-7-yl)sulfonium trifluoromethanesulfonate, diphenyl(coumarin-2-thione-7-yl)sulfonium nonafluorobutanesulfonate and diphenyl(coumarin-2-thione-7-yl)sulfonium p-toluenesulfonate.

The preferable specific example shown by the general formula [39] includes, for example, bis(xanthene-9-one-2-yl)iodonium chloride, bis(xanthene-9-one-2-yl)iodonium bromide, bis(xanthene-9-one-2-yl)iodonium perchlorate, bis(xanthene-9-one-2-yl)iodonium tetrafluoroborate, bis(xanthene-9-one-2-yl)iodonium hexafluorophosphate, bis(xanthene-9-one-2-yl)iodonium hexafluoroarsenate, bis(xanthene-9-one-2-yl)iodonium hexafluoroantimonate, bis(xanthene-9-one-2-yl)iodonium tetraphenylborate, bis(xanthene-9-one-2-yl)iodonium tetrakis{3,5-bis(trifluoromethyl)phenyl)borate, bis(xanthene-9-one-2-yl)iodonium tetrakis(pentafluorophenyl)borate, bis(xanthene-9-one-2-yl)iodonium tetraphenylgallate, bis(xanthene-9-one-2-yl)iodonium tetrakis(pentafluorophenyl)gallate, bis(xanthene-9-one-2-yl)iodonium trifluoromethanesulfonate, bis(xanthene-9-one-2-yl)iodonium nonafluorobutanesulfonate, bis(xanthene-9-one-2-yl)iodonium perfluorooctanesulfonate, bis(xanthene-9-one-2-yl)iodonium benzenesulfonate, bis(xanthene-9-one-2-yl)iodonium p-toluenesulfonate, bis(xanthene-9-one-2-yl)iodonium 4-dodecylbenzenesulfonate, bis(xanthene-9-one-2-yl)iodonium 4-fluorobenzenesulfonate, bis(xanthene-9-one-2-yl)iodonium 2,4-difluorobenzenesulfonate, bis(xanthene-9-one-2-yl)iodonium pentafluorobenzenesulfonate, bis(xanthene-9-one-2-yl)iodonium 4-trifluoromethylbenzenesulfonate, bis(xanthene-9-one-2-yl)iodonium 3,5-bis(trifluoromethyl)benzenesulfonate, bis(xanthene-9-one-2-yl)iodonium acetate, bis(xanthene-9-one-2-yl)iodonium pentafluorobutanoate, bis(xanthene-9-one-2-yl)iodonium perfluorooctanoate and bis(xanthene-9-one-2-yl)iodonium perfluorododecanoate, and among others, a preferable one includes, for example, bis(xanthene-9-one-2-yl)iodonium hexafluorophosphate, bis(xanthene-9-one-2-yl)iodonium tetraphenylborate, bis(xanthene-9-one-2-yl)iodonium trifluoromethanesulfonate, bis(xanthene-9-one-2-yl)iodonium nonafluorobutanesulfonate and bis(xanthene-9-one-2-yl)iodonium p-toluenesulfonate, a more preferable one includes bis(xanthene-9-one-2-yl)iodonium hexafluorophosphate.

The preferable specific example shown by the general formula [40] includes, for example, bis(coumarin-7-yl)iodonium chloride, bis(coumarin-7-yl)iodonium bromide, bis(coumarin-7-yl)iodonium perchlorate, bis(coumarin-7-yl)iodonium tetrafluoroborate, bis(coumarin-7-yl)iodonium hexafluorophosphate, bis(coumarin-7-yl)iodonium hexafluoroarsenate, bis(coumarin-7-yl)iodonium hexafluoroantimonate, bis(coumarin-7-yl)iodonium tetraphenylborate, bis(coumarin-7-yl)iodonium tetrakis{(3,5-bis(trifluoromethyl)phenyl}borate, bis(coumarin-7-yl)iodonium tetrakis(pentafluorophenyl)borate, bis(coumarin-7-yl)iodonium tetraphenylgallate, bis(coumarin-7-yl)iodonium tetrakis(pentafluorophenyl)gallate, bis(coumarin-7-yl)iodonium trifluoromethanesulfonate, bis(coumarin-7-yl)iodonium nonafluorobutanesulfonate, bis(coumarin-7-yl)iodonium perfluorooctanesulfonate, bis(coumarin-7-yl)iodonium benzenesulfonate, bis(coumarin-7-yl)iodonium p-toluenesulfonate, bis(coumarin-7-yl)iodonium 4-dodecylbenzenesulfonate, bis(coumarin-7-yl)iodonium 4-fluorobenzenesulfonate, bis(coumarin-7-yl)iodonium 2,4-difluorobenzenesulfonate, bis(coumarin-7-yl)iodonium pentafluorobenzenesulfonate, bis(coumarin-7-yl)iodonium 4-trifluoromethylbenzenesulfonate, bis(coumarin-7-yl)iodonium 3,5-bis(trifluoromethyl)benzenesulfonate, bis(coumarin-7-yl)iodonium acetate, bis(coumarin-7-yl)iodonium pentafluorobutanoate, bis(coumarin-7-yl)iodonium perfluorooctanoate and bis(coumarin-7-yl)iodonium perfluorododecanate, and among others, a preferable one includes, for example, bis(coumarin-7-yl)iodonium hexafluorophosphate, bis(coumarin-7-yl)iodonium tetraphenylborate, bis(coumarin-7-yl)iodonium trifluoromethanesulfonate, bis(coumarin-7-yl)iodonium nonafluorobutanesulfonate and bis(coumarin-7-yl)iodonium p-toluenesulfonate.

The preferable specific example shown by the general formula [41] includes, for example, (coumarin-7-yl)(xanthene-9-one-2-yl)iodonium chloride, (coumarin-7-yl)(xanthene-9-one-2-yl)iodonium bromide, (coumarin-7-yl) (xanthene-9-one-2-yl)iodonium tetrafluoroborate, (coumarin-7-yl)(xanthene-9-one-2-yl)iodonium hexafluorophosphate, (coumarin-7-yl)(xanthene-9-one-2-yl)iodonium hexafluoroarsenate, (coumarin-7-yl)(xanthene-9-one-2-yl)iodonium hexafluoroantimonate, (coumarin-7-yl) (xanthene-9-one-2-yl)iodonium tetraphenylgallate, (coumarin-7-yl)(xanthene-9-one-2-yl)iodonium tetraphenylborate, (coumarin-7-yl)(xanthene-9-one-2-yl)iodonium tetrakis{3,5-bis(trifluoromethyl)phenyl}borate, (coumarin-7-yl)(xanthene-9-one-2-yl)iodonium tetrakis(pentafluorophenyl)borate, (coumarin-7-yl)(xanthene-9-one-2-yl)iodonium tetraphenylgallate, (coumarin-7-yl)(xanthene-9-one-2-yl)iodonium tetrakis(pentafluorophenyl)gallate, (coumarin-7-yl)(xanthene-9-one-2-yl)iodonium, trifluoromethanesulfonate, (coumarin-7-yl)(xanthene-9-one-2-yl)iodonium nonafluorobutanesulfonate, (coumarin-7-yl)(xanthene-9-one-2-yl)iodonium perfluorooctanesulfonate, (coumarin-7-yl)(xanthene-9-one-2-yl)iodonium benzenesulfonate, (coumarin-7-yl) (xanthene-9-one-2-yl)iodonium p-toluenesulfonate, (coumarin-7-yl) (xanthene-9-one-2-yl)iodonium 4-dodecylbenzenesulfonate, (coumarin-7-yl)(xanthene-9-one-2-yl)iodonium 4-fluorobenzenesulfonate, (coumarin-7-yl)(xanthene-9-one-2-yl)iodonium 2,4-difluorobenzenesulfonate, (coumarin-7-yl)(xanthene-9-one-2-yl)iodonium pentafluorobenzenesulfonate, (coumarin-7-yl)(xanthene-9-one-2-yl) iodonium 4-trifluoromethylbenzenesulfonate, (coumarin-7-yl)(xanthene-9-one-2-yl)iodonium 3,5-bis(trifluoromethyl)benzenesulfonate, (coumarin-7-yl)(xanthene-9-one-2-yl) iodonium acetate, (coumarin-7-yl)(xanthene-9-one-2-yl) iodonium pentafluorobutanoate, (coumarin-7-yl)(xanthene-9-one-2-yl)iodonium perfluorooctanoate and (coumarin-7-yl) (xanthene-9-one-2-yl)iodonium perfluorododecanoate, and among others, a preferable one includes, for example, (coumarin-7-yl) (xanthene-9-one-2-yl)iodonium hexafluorophosphate, (coumarin-7-yl)(xanthene-9-one-2-yl)iodonium tetraphenylborate, (coumarin-7-yl)(xanthene-9-one-2-yl)iodonium trifluoromethanesulfonate, (coumarin-7-yl) (xanthene-9-one-2-yl)iodonium nonafluorobutanesulfonate, (coumarin-7-yl)(xanthene-9-one-2-yl)iodonium p-toluenesulfonate, and a more preferable one includes (coumarin-7-yl)(xanthene-9-one-2-yl)iodonium hexafluorophosphate.

The preferable specific example shown by the general formula [42] includes, for example, 2-(phenyliodonio)xanthene-9-one hexafluorophosphate, 2-(phenyliodonio)xanthene-9-one hexafluoroarsenate, 2-(phenyliodonio)xanthene-9-one hexafluoroantimonate, 2-(phenyliodonio)xanthene-9-one tetrafluoroborate, 2-(phenyliodonio)xanthene-9-one tetrakis{3,5-bis(trimethyl)phenyl}borate, 2-(phenyliodonio)xanthene-9-one tetrakis(pentafluorophenyl)borate, 2-(phenyliodonio)xanthene-9-one tetraphenylgallate, 2-(phenyliodonio)xanthene-9-one trifluoromethanesulfonate, 2-(phenyliodonio)xanthene-9-one nonafluorobutanesulfonate, 2-(phenyliodonio)xanthene-9-one perfluorooctanesulfonate, 2-(phenyliodonio)xanthene-9-one benzenesulfonate, 2-(phenyliodonio)xanthene-9-one p-toluenesulfonate, 2-(phenyliodonio)xanthene-9-one p-dodecylbenzenesulfonate, 2-(phenyliodonio)xanthene-9-one 4-fluorobenzenesulfonate, 2-(phenyliodonio)xanthene-9-one 2,4-difluorobenzenesulfonate, 2-(phenyliodonio)xanthene-9-one pentafluorobenzenesulfonate, 2-(phenyliodonio)xanthene-9-one acetate, 2-(phenyliodonio)xanthene-9-one pentafluorobutanoate, 2-(phenyliodonio)xanthene-9-one perfluorooctanoate and 2-(phenyliodonio)xanthene-9-one perfluorodecanoate, and among others a preferable one includes, for example, 2-(phenyliodonio)xanthene-9-one hexafluorophosphate, 2-(phenyliodonio)xanthene-9-one tetraphenylborate, 2-(phenyliodonio)xanthene-9-one trifluoromethanesulfonate, 2-(phenyliodonio)xanthene-9-one nonafluorobutanesulfonate and 2-(phenyliodonio)xanthene-9-one p-toluenesulfonate, and a more preferable one includes 2-(phenyliodonio)xanthene-9-one hexafluorophosphate.

The preferable specific example shown by the general formula [43] includes, for example, 7-(phenyliodonio)coumarin hexafluorophosphate, 7-(phenyliodonio) coumarin hexafluoroarsenate, 7-(phenyliodonio)coumarin hexafluoroantimonate, 7-(phenyliodonio)coumarin tetraphenylborate, 7-(phenyliodonio)coumarin trifluoromethanesulfonate, 7-(phenyliodonio)coumarin nonafluorobutanesulfonate, 7-(phenyliodonio)coumarin p-toluenesulfonate, 7-(p-methylphenyliodonio)coumarin hexafluorophosphate, 7-(p-methylphenyliodonio)coumarin hexafluoroarsenate, 7-(p-methylphenyliodonio)coumarin hexafluoroantimonate, 7-(p-methylphenyliodonio)coumarin tetraphenylborate, 7-(p-methylphenyliodonio)coumarin trifluoromethanesulfonate, 7-(phenyliodonio)coumarin nonafluorobutanesulfonate and 7-(p-methylphenyliodonio)coumarin p-toluenesulfonate and among others, for example, 7-(phenyliodonio)coumarin hexafluorophosphate is preferable.

The sulfonium salt shown by the general formula [1] can be synthesized by, for example, the following [A], [B] and [C] methods.

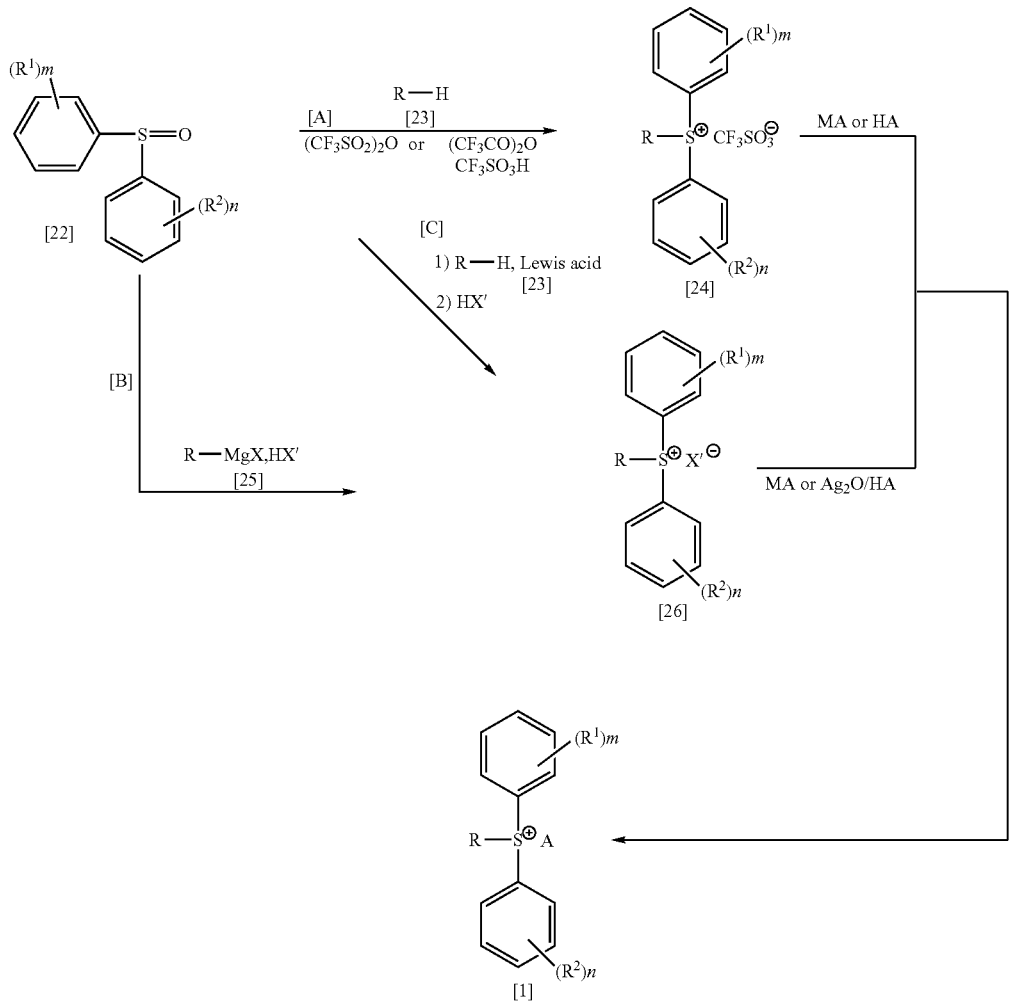
(wherein M is a metal atom; X and X' is a halogen atom; and R, $R^1$, $R^2$, A, m and n have the same meaning as above).
The iodonium salt shown by the general formula [35] can be synthesized by, for example, the following [D], [E] and [F] methods.
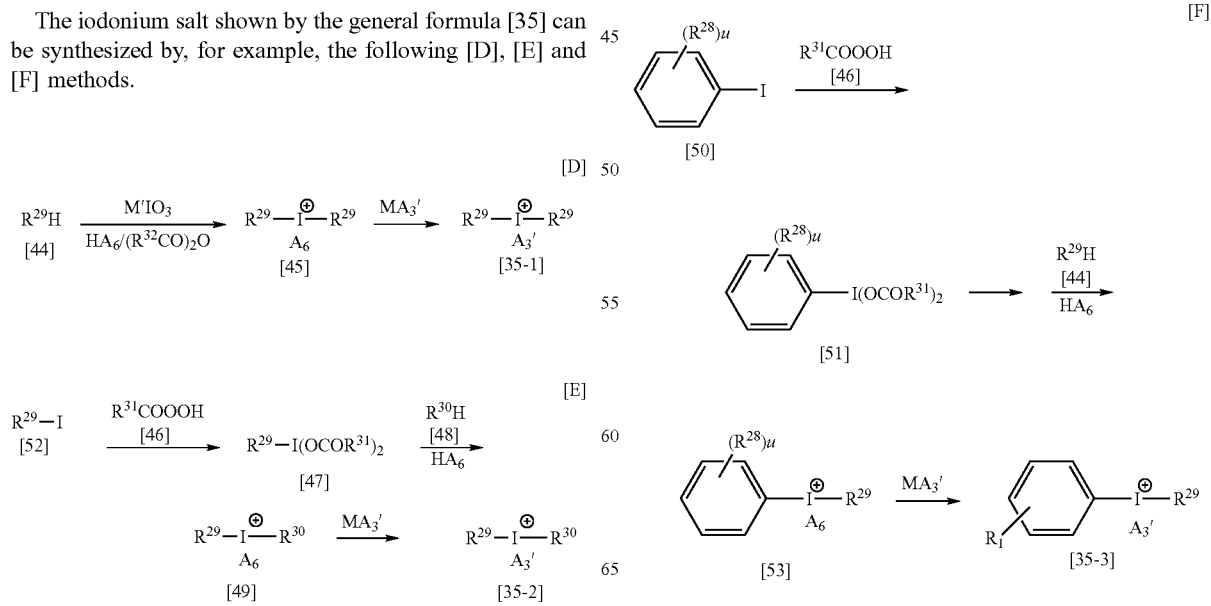

(wherein one of $R^{29}$ and $R^{30}$ is a group shown by the general formula [2] and the other is a group shown by the general formula [3]; $R^{31}$ is a lower alkyl group or a lower haloalkyl group; $R^{32}$ is a lower alkyl group or a lower haloalkyl group; M' is an alkali metal atom; $A^6$ is a halogen atom, a hydrogen sulfate ion or an anion derived from a perfluoroalkylcarboxylic acid; $A_3$' is an objective anion; and $R^{28}$, M and u have the same meaning as above.)

The metal atom shown by M includes, for example, a silver atom, a lithium atom, a sodium atom, a potassium atom, a rubidium atom and a cesium atom, and among others, a silver atom is preferable.

The halogen atom shown by X and X' includes, for example, a fluorine atom, a chlorine atom, a bromine atom and an iodine atom.

The alkali metal atom shown by M' includes, for example, a lithium atom, a sodium atom, a potassium atom, a rubidium atom and a cesium atom, and among others, a lithium atom, a sodium atom and a potassium atom are preferable.

The lower alkyl group shown by $R^{31}$ and $R^{32}$ may be straight chained, branched or cyclic and includes one having generally 1 to 6, preferably 1 to 4 carbon atoms, which is specifically exemplified by the same as examples of the alkyl group having 1 to 6 carbon atoms among the alkyl group which may have a halogen atom or an aryl group as a substituent, shown by the above-mentioned $R^1$ to $R^6$ and among others, a preferable one includes, for example, a methyl group, an ethyl group, a n-propyl group, an isopropyl group, a n-butyl group, an isobutyl group, a sec-butyl group and a tert-butyl group and a more preferable one includes a methyl group and an ethyl group.

The lower haloalkyl group shown by $R^{31}$ and $R^{32}$ may be straight chained, branched or cyclic, and includes one, wherein a part of or all of hydrogen atoms of the lower alkyl group having generally 1 to 6, preferably 1 to 4 carbon atoms, shown by the above-mentioned $R^3$ are substituted by a halogen atom (e.g. a fluorine atom, a chlorine atom, a bromine atom and an iodine atom), which is specifically exemplified by the same as examples of the lower haloalkyl group as the substituent of the aryl group which may have a substituent selected from a lower haloalkyl group, a halogen atom, a nitro group and a cyano group, shown by the above-mentioned $R^7$, and among others, a trifluoromethyl group and a pentafluoroethyl group are preferable.

The halogen atom shown by $A_6$ includes, for example, a fluorine atom, a chlorine atom, a bromine atom and an iodine atom, and among others, a chlorine atom and a bromine atom are preferable.

The anion derived from the perfluoroalkylcarboxylic acid shown by $A_6$ includes, for example, one derived from a trifluoroacetic acid and a pentafluoropropionic acid.

The peracid shown by the general formula [46] includes, for example, peracetic acid, perpropionic acid and trifluoroperacetic acid. Those peracid may be a commercial product or suitably be synthesized according to common methods such as a reaction of carboxylic anhydrides such as acetic anhydride, propionic anhydride and trifluoroacetic anhydride with hydrogen peroxide.

The compound shown by the general formulae [23], [25], [44], [48], [50] and [52] may be a commercial product or may suitably be synthesized according to common methods.

Namely, a synthesis method for a sulfonium salt of the present invention is explained in detail.

In a method [A], a sulfoxide shown by the general formula [22], synthesized by a common method (see Ber., 23, 1844 (1890), J. Chem. Soc. (C), 2424 (1969)) is dissolved in a solvent such as ethers including ethyl ether, isopropyl ether, tetrahydrofuran and 1,2-dimethoxyethane; hydrocarbons including hexane and heptane; and aromatic hydrocarbons including benzene and nitrobenzene, or a mixed solvent consisting of the above solvent and halogenated hydrocarbons such as methylene chloride, methylene bromide, 1,2-dichloroethane and chloroform, and a compound shown by the general formula [23] in an amount of 1 to 10 mole parts, (hereinafter in the description on methods [A], [B] and [C], "mole parts", means how many mole parts relative to 1 mole part of a raw compound such as a sulfoxide shown by the general formula [22]), trifluoromethanesulfonic anhydride in an amount of 1 to 3 mole parts of, or trifluoromethane sulfonic acid in an amount of 1 to 3 mole parts, and trifluoroacetic anhydride in an amount of 1 to 3 mole parts, relative to the sulfoxide shown by the general formula [22], are added thereto at −80 to 30° C., followed by allowing a reaction to take place at −80 to 30° C. for 0.5 to 10 hours with stirring to obtain a compound shown by the general formula [24]. Then, the obtained compound shown by the general formula [24] is dissolved in an aqueous solution of an alcohol such as methanol, ethanol and isopropanol, and treated with an anion exchange resin, and then an acid (HA) in an amount of 0.9 to 1.5 mole parts is added thereto. After removing the alcohol, the resultant is redissolved in an organic solvent such as methylene chloride, 1,2-dichloroethane, ethyl acetate, butyl acetate, propylene glycol monomethyl ether acetate, methyl isobutyl ketone and methyl ethyl ketone, followed by washing with water and concentrating under reduced pressure to obtain the compound of the present invention, shown by the general formula [1]. In another method, the obtained compound shown by the general formula [24] is dissolved in an organic solvent such as methylene chloride, 1,2-dichloroethane, ethyl acetate, butyl acetate, propylene glycol monomethyl ether acetate, methyl isobutyl ketone and methyl ethyl ketone, and an acid salt (MA) in an amount of 0.9 to 1.5 mole parts is added thereto, followed by allowing a reaction to take place at 5 to 30° C. for 0.5 to 10 hours with stirring, removing a water layer, washing with water and concentrating under reduced pressure to obtain the compound shown by the general formula [1].

In a method [B], a sulfoxide shown by the general formula [22] is dissolved in ethers such as ethyl ether, isopropyl ether, tetrahydrofuran and 1,2-dimethyl ether or a mixed solvent consisting of the ethers and halogenated hydrocarbons such as methylene chloride, methylene bromide, 1,2-dichloroethane and chloroform or aromatic hydrocarbons such as benzene, toluene and xylene, and Grignard reagent (RMgX) in an amount of 0.5 to 3 mole parts, shown by the general formula [25] is added thereto, if necessary, in the presence of a catalyst such as trimethylsilyl triflate and trimethylsilyl chloride at −70 to 50° C., followed by allowing a reaction to take place at −70 to 50° C. for 0.5 to 10 hours with stirring. After completion of the reaction, the reaction solution is treated with an aqueous solution of hydrohalic acid (HX') such as an aqueous solution of hydrobromic acid, hydrochloric acid and hydroiodic acid to obtain a compound shown by the general formula [26]. Then, the obtained compound is dissolved in alcohols such as methanol, ethanol and isopropanol, followed by treatment with silver oxide, an acid (HA) in an amount of 0.9 to 1.5 mole parts is added thereto. After removing the alcohol, the resultant is redissolved in an organic solvent such as methylene chloride, 1,2-dichloroethane, ethyl acetate, butyl acetate, propylene glycol monomethyl ether acetate, methyl isobutyl ketone and methyl ethyl ketone, followed by washing with water and concentrating under reduced pressure to obtain a compound of the present invention, shown by the general formula [1]. In another method, the obtained compound shown by the general formula [26] is dissolved in an organic solvent such as methylene chloride, 1,2-dichloroethane, ethyl acetate, butyl acetate, propylene glycol monomethyl ether acetate, methyl isobutyl ketone and methyl ethyl ketone, and an aqueous solution of an acid salt (MA) in an amount of 0.9 to 1.5 mole parts is added thereto, followed by allowing a reaction to take place at 5 to 30° C. for 0.5 to 10 hours with stirring, removing a water layer, washing with water and concentrating under reduced pressure to obtain the compound of the present invention, shown by the general formula [1].

In a method [C], a compound shown by the general formula [22] is reacted with a compound shown by the general formula [23] in an amount of 1 to 50 mole parts and Lewis acid such as a halogenated aluminum (e.g. aluminum chloride, aluminum bromide and aluminum iodide), a halogenated boron (e.g. boron trifluoride and boron tribromide) and a trihalogenated metal (e.g. iron trichloride, iron tribromide, titanium tribromide, titanium trichloride and titanium tribromide) in an amount of 1 to 10 mole parts at −20 to 180° C. for 0.5 to 24 hours with stirring, followed by treating with an aqueous solution of hydrohalic acid (HX) such as an aqueous solution of hydrobromic acid, hydrochloric acid and hydroiodic acid to obtain the compound shown by the general formula [26]. Then, the obtained compound is dissolved in alcohols such as methanol, ethanol and isopropanol, and treated with silver oxide, and then an acid (HA) in an amount of 0.9 to 1.5 mole parts is added thereto. After removing the alcohol, redissolving in an organic solvent such as methylene chloride, 1,2-dichloroethane, ethyl acetate, butyl acetate, propylene glycol monomethyl ether acetate, methyl isobutyl ketone and methyl ethyl ketone, washing with water and concentrating under reduced pressure to obtain the compound of the present invention, shown by the general formula [1]. In another method, the obtained compound shown by the general formula [26] is dissolved in an organic solvent such as methylene chloride, 1,2-dichloroethane, ethyl acetate, butyl acetate, propylene glycol monomethyl ether acetate, methyl isobutyl ketone and methyl ethyl ketone, and an aqueous solution of an acid salt (MA) in an amount of 0.9 to 1.5 mole parts is added thereto, followed by allowing a reaction to take place at 5 to 30° C. for 0.5 to 10 hours with stirring, removing a water layer, washing with water and concentrating under reduced pressure to obtain the compound of the present invention, shown by the general formula [1].

Compounds shown by the general formulae [24] and [26], obtained by the above-mentioned methods [A], [B] and [C] are also included in sulfonium salts of the present invention, shown by the general formula [1].

Further, a synthesis method for an iodonium salt of the present invention is explained described bellow in detail.

In a method [D], a heterocycle-containing aromatic compound shown by the general formula [44] is dissolved in carboxylic anhydrides such as acetic anhydride and propionic anhydride or a mixed solvent consisting of the carboxylic anhydrides and halogenated hydrocarbons such as methylene chloride, methylene bromide, 1,2-dichloroethane and chloroform, and an iodate salt (M'IO$_3$) in an amount of 0.4 to 0.6 mole parts, relative to the compound shown by the general formula [44] (hereinafter in the description on methods [D], [E] and [F], "mole parts" means how many mole parts relative to 1 mole part of the raw compound shown by the general formula [44]) at −70 to 30° C., and then a compound (HA$_6$) such as concentrated sulfuric acid in an amount of 1 to 10 times moles of or a mixed acid consisting of the HA$_6$ and a carboxylic anhydride such as acetic anhydride, propionic anhydride, trifluoroacetic anhydride is added dropwise thereto at −70 to 30° C. for 0.5 to 10 hours, followed by allowing a reaction to take place at −70 to 30° C. for 0.5 to 10 hours with stirring. After completion of the reaction, the reaction solution is poured at 0 to 30° C. into ice water, followed by extracting with halogenated hydrocarbons such as methylene chloride, methylene bromide, 1,2-dichloroethane and chloroform, and concentrating to obtain a compound shown by the general formula [45]. Then the obtained compound shown by the general formula [45] is dissolved in halogenated hydrocarbons such as methylene chloride, methylene bromide, 1,2-dichloroethane and chloroform, and an aqueous solution of a compound (MA$_3$') in an amount of 1 to 10 mole parts is poured thereto, followed by allowing a reaction to take place at 0 to 30° C. for 0.5 to 10 hours with stirring to obtain an iodonium salt having a desired counter anion A$_3$', shown by the general formula [35-1].

In a method [E], an iodized heterocycle-containing aromatic compound shown by the general formula [52] is reacted with a peracid shown by the general formula [46] to synthesize a compound shown by the general formula [47]. Then the obtained compound shown by the general formula [47] is dissolved in carboxylic anhydrides such as acetic anhydride and propionic anhydride, or a mixed solvent consisting of the carboxylic anhydrides and halogenated hydrocarbons such as methylene chloride, methylene bromide, 1,2-dichloroethane and chloroform, and a heterocycle-containing aromatic compound shown by the general formula [48], in an amount of 1 to 10 mole parts is added thereto at −80 to 30° C., and then a compound (HA$_6$) in an amount of 1 to 10 mole parts is added dropwise thereto at −80 to 30° C. for 0.5 to 10 hours, followed by allowing a reaction to take place at −80 to 30° C. for 0.5 to 10 hours with stirring to obtain a compound shown by the general formula [49]. Then the obtained compound shown by the general formula [49] is dissolved in halogenated hydrocarbons such as methylene chloride, methylene bromide, 1,2-dichloroethane and chloroform, and a solution of a compound (MA$_3$') in an amount of 1 to 10 mole parts is poured thereto, followed by allowing a reaction to take place at 0 to 30° C. for 0.5 to 10 hours with stirring to obtain an iodonium salt having a desired counter anion A$_3$', shown by the general formula [35-2].

In a method [F], an iodoaryl compound shown by the general formula [50] is reacted with a peracid shown by the general formula [46] to synthesize a compound shown by the general formula [51]. Then a heterocycle-containing aromatic compound shown by the general formula [44] is dissolved in carboxylic anhydrides such as acetic anhydride and propionic anhydride or a mixed solvent consisting of the carboxylic anhydrides and halogenated hydrocarbons such as methylene chloride, methylene bromide, 1,2-dichloroethane and chloroform, and a compound shown by the general formula [51] in an amount of 1 to 10 mole parts is added thereto at −80 to 30° C., and then a compound (HA$_6$) in an amount of 1 to 10 mole parts is added dropwise thereto at −80 to 30° C. for 0.5 to 10 hours, followed by allowing a reaction to take place at −80 to 30° C. for 0.5 to 10 hours with stirring to obtain a compound shown by the general formula [53]. Then the obtained compound shown by the general formula [53] is dissolved in halogenated hydrocarbons such as methylene chloride, methylene bromide, 1,2-dichloroethane and chloroform, and then a solution of a compound (MA$_3$') in an amount of 1 to 10 mole parts is poured thereto, followed by allowing a reaction to take place at 0 to 30° C. for 0.5 to 10 hours with stirring to obtain an iodonium salt having a desired counter anion A$_3$', shown by the general formula [35-3].

Compounds shown by the general formulae [45], [49] and [53], obtained by the above-mentioned methods [D], [E] and [F] and are also included in iodonium salts of the present invention, shown by the general formula [35].

Among sulfonium salts of the present invention, shown by the general formula [1] and iodnium salts of the present invention, shown by the general formula [35], those with a halogen atom as an anion, shown by A and A$_3$ are useful as raw materials for various onium salts of the present invention, on the other hand, those with an anion derived from an inorganic strong acid, a sulfonic acid and a compound shown by the above-mentioned general formula [4] are useful as cationic photopolymerization initiators and those with an anion derived from an inorganic strong acid, an organic acid and a compound shown by the above-mentioned general formula [4] have superior effects as acid generators composing a resist composition used for manufacturing liquid crystal panel, various semiconductor elements and printed circuit boards, and printing materials such as PS boards and CTP boards.

<1> First, use of a sulfonium salt and an iodnium salt of the present invention as a cationic photopolymerization initiator will be explained.

The preferable sulfonium salt of the present invention useful as a cationic photopolymerization initiator includes, for example, one shown by the general formula [8]:

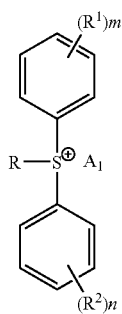

[8]

(wherein A$_1$ is an anion derived from an inorganic strong acid, a sulfonic acid or a compound shown by the above-mentioned general formula [4]; and R, R$^1$, R$^2$, m and n have the same meaning as above.), and among others, sulfonium salts wherein A$_1$ is an anion derived from a compound shown by the general formulae [4] and [5] are preferable.

The preferable iodonium salt of the present invention useful as a cationic photopolymerization initiator includes, for example, one shown by the general formula [37]:

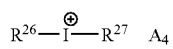

[37]

(wherein A$_4$ is an anion derived from an inorganic strong acid, a sulfonic acid or a compound shown by the general formula [4]; and R$^{26}$, R$^{27}$ and others are the same as described above), and among others, iodonium salts wherein A$_4$ is an anion derived from a compound-shown by the general formulae [4] and [5] are preferable.

The sulfonium salt and the iodonium salt of the present invention (hereinafter collectively abbreviated as onium salts) generate an acid by irradiation with light, whereby polymerization rapidly proceeds if a various kind of epoxy monomers or vinyl ether monomers exist in the reaction system.

Polymerization or copolymerization of an epoxy monomer or a vinyl ether monomer by using the onium salt of the present invention, shown by the general formula [8] or [37], as a polymerization initiator can be performed by a common polymerization reaction of the onium salt of the present invention, shown by the general formula [8] or [37], and these various monomers in a suitable solvent or without using a solvent under inert gas atmosphere, if necessary.

The epoxy monomer includes, for example, one shown by the general formula [27]:

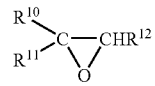

[27]

[wherein R$^{10}$ and R$^{11}$ are each independently a hydrogen atom, a lower alkyl group, an aryl group or a carboxyl group; R$^{12}$ is a hydrogen atom, an alkyl group, a lower haloalkyl group, a lower hydroxyalkyl group, an aryl group, a lower alkoxycarbonyl group, a carboxyl group, a group shown by the general formula [28]:

—CH$_2$-E-R$^{13}$ [28]

(wherein E is an oxygen atom or a —OCO— group; and R$^{13}$ is an alkyl group, a lower alkenyl group or an aryl group), an epoxyethyl group or an epoxycyclohexyl group; and R$^{10}$ and R$^{12}$ may form an aliphatic ring together with the adjacent carbon atoms] and one shown by the general formula [29]:

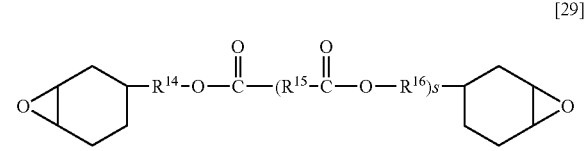

[29]

(wherein R$^{14}$ to R$^{16}$ are each independently a lower alkylene chain; and s is an integer of 0 or 1).

In the general formula [27], the lower alkyl group shown by R$^{10}$ and R$^{11}$ may be straight chained, branched or cyclic, and includes one having generally 1 to 6, preferably 1 to 3 carbon atoms, which is specifically exemplified by a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a cyclopropyl group, a cyclobutyl group, a cyclopentyl group and a cyclohexyl group.

In the general formulae [27] and [28], the aryl group shown by R$^{10}$ to R$^{13}$ includes one having generally 6 to 15, preferably 6 to 10 carbon atoms, which is specifically exemplified by a phenyl group, a naphtyl group, an anthryl group and a phenanthryl group.

The alkyl group shown by $R^{12}$ and $R^{13}$ may be straight chained, branched or cyclic, and includes one having generally 1 to 18, preferably 1 to 16 carbon atoms, which is specifically exemplified by the same as ecamples of the lower alkyl group shown by $R^{10}$ and $R^{11}$, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a n-hexadecyl group, an isohexadecyl group, a sec-hexadecyl group, a tert-hexadecyl group, a neohexadecyl group, a n-heptadecyl group, an isoheptadecyl group, a sec-heptadecyl group, a tert-heptadecyl group, a neoheptadecyl group, a n-octadecyl group, an isooctadecyl group, a sec-octadecyl group, a tert-octadecyl group, a neooctadecyl group, a cycloheptyl group, a cyclooctyl group, a cyclononyl-group and a cyclodecyl group.

In the general formula [27], the lower haloalkyl group shown by $R^{12}$ includes one, wherein a part of or all of the hydrogen atoms of the lower alkyl group having 1 to 6, preferably 1 to 3 carbon atoms, shown by the above-mentioned $R^{10}$ and $R^{11}$, are substituted by a halogen atom (e.g. a fluorine atom, a chlorine atom, a bromine atom and an iodine atom), which is specifically exemplified by a fluoromethyl group, a chloromethyl group, a bromomethyl group, an iodomethyl group, a difluoromethyl group, a dichloromethyl group, a trifluoromethyl group, a trichloromethyl group, a tribromomethyl group, a triiodomethyl group, a pentafluoroethyl group, a pentachloroethyl group, a pentabromoethyl group, a pentaiodoethyl group, a heptafluoropropyl group, a heptachloropropyl group, a heptabromopropyl group, a heptaiodopropyl group, a nonafluorobutyl group, a nonachlorobutyl group, a nonabromobutyl group, a nonaiodobutyl group, a perfluoropentyl group, a perchloropentyl group, a perfluorohexyl group and a perchlorohexyl group.

The lower hydroxyalkyl group shown by $R^{12}$ includes one, wherein the terminal hydrogen atom of the lower alkyl group shown by the above-mentioned $R^{10}$ and $R^{11}$, is substituted by a hydroxyl group.

The lower alkoxycarbonyl group shown by $R^{12}$ may be straight chained, branched or cyclic, and includes one having generally 2 to 7, preferably 2 to 4 carbon atoms, which is specifically exemplified by a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentyloxycarbonyl group, an isopentyloxycarbonyl group, a sec-pentyloxycarbonyl group, a tert-pentyloxycarbonyl group, a neopentyloxycarbonyl group, a n-hexyloxycarbonyl group, an isohexyloxycarbonyl group, a sec-hexyloxycarbonyl group, a tert-hexyloxycarbonyl group, a neohexyloxycarbonyl group, a cyclopropyloxycarbonyl group, a cyclobutyloxycarbonyl group, a cyclopentyloxycarbonyl group and a cyclohexyloxycarbonyl group.

In the general formula [28], the lower alkenyl group shown by $R^{13}$ may be straight chained, branched or cyclic, and includes one having generally 2 to 6, preferably 2 to 3 carbon atoms, which is specifically exemplified by a vinyl group, an allyl group, a 1-propenyl group, an isopropenyl group, a 1-butenyl group, a 2-butenyl group, a 3-butenyl group, a 2-methylallyl group, a 1-pentenyl group, a 2-pentenyl group, a 3-pentenyl group, a 4-pentenyl group, a 2-methy-2-butenyl group, a 1-hexenyl group, a 2-hexenyl group, a 3-hexenyl group, a 5-hexenyl group, a 2-methyl-2-pentenyl group, a 1-cyclobutenyl group, a 1-cyclopentenyl group and a 1-cyclohexenyl group.

The case where $R^{10}$ and $R^{12}$ form an aliphatic ring together with the adjacent carbon atoms includes a case where a saturated aliphatic ring having 5 to 10 carbon atoms is formed. The specific example s of these rings are a cyclopentane ring, a cyclohexane ring, a cycloheptane ring, a cyclooctane ring, a cyclononane ring and a cyclodecane ring. These aliphatic rings may further be condensed with an aromatic ring such as a benzene ring or a naphthalene ring.

In the general formula [29], the lower alkelene chain shown by $R^{14}$ to $R^{16}$ includes one having generally 1 to 6, preferably 1 to 4 carbon atoms, which is specifically exemplified by a methylene group, an ethylene group, a trimethylene group, a tetramethylene group, a pentamethylene group and a hexamethylene group.

The vinyl ether group includes one shown by the general formula [31]:

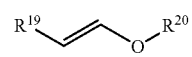

[31]

[wherein $R^{19}$ is a hydrogen atom or a lower alkyl group; and $R^{20}$ is an alkyl group, a group shown by the formula [32]:

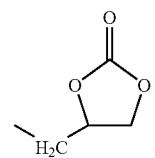

[32]

or a group shown by the general formula [33]:

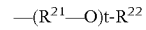

[33]

(where $R^{21}$ is an alkylenen group; $R^{22}$ is a hydrogen atom or a vinyl group; and t is an integer of 1 to 3.)

In the general formula [31], the lower alkyl group shown by $R^{19}$ may be straight chained, branched or cyclic and includes one having generally 1 to 6 carbon atoms, which is specifically exemplified by a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 2-methylbutyl group, a 1-ethylpropyl group, a n-hexyl group, an isohexyl group, a sec-hexyl group, a tert-hexyl group, a neohexyl group, a 2-methylpentyl group, a 3-methylpentyl group, a 1,2-dimethylbutyl group, a 2,2-dimethylbutyl group, a 1-ethylbutyl group, a 2-ethylbutyl group, a cyclopropyl group, a cyclobutyl group, a cyclopentyl group and a cyclohexyl group.

The alkyl group shown by $R^{20}$ may be straight chained, branched or cyclic, and includes one having generally 1 to 15, preferably 1 to 12 carbon atoms, which is specifically exemplified by a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a cyclopropyl group, a cyclobutyl group, a cyclopentyl group, a cyclohexyl group, a cycloheptyl group, a cyclooctyl group, a cyclononyl group and a cyclodecyl group.

In the general formula [33], the alkylene group shown by $R^{21}$ may be straight chained, branched or cyclic, and includes one having generally 2 to 10, preferably 2 to 8 carbon atoms, which is specifically exemplified by linear alkylene groups such as a methylene group, an ethylene group, a trimethylene group, a tetramethylene group, a pentamethylene group, a hexamethylene group, a heptamethylene group, an octamethylene group, a nonamethylene group and a decamethylene group; branched alkylene groups such as n ethylidene group, a propylene group, an isopropylidene group, a 1-methyltrimethylene group, a 2-methyltrimethylene group, a 1,1-dimethylethylene group, a 1,2-dimethylethylene group, an ethylethylene group, a 1-methyltetramethylene group, a 1,1-dimethyltrimethylene group, a 2,2-dimethyltrimethylene group, a 2-ethyltrimethylene group, a 1-methylpentamethylene group, a 2-methylpentamethylene group, a 1,3-dimethyltetramethylene group, a 3-ethyltetramethylene group, a 1-methylhexamethylene group, a 1-methylheptamethylene group, a 1,4-diethyltetramethylene group, a 2,4-dimethylheptamethylene group, a 1-methyloctamethylene group and a 1-methylnonamethylene group; and cyclic alkylene groups such as a cyclopropylene group, a 1,3-cyclobutylene group, a 1,3-cyclopentylene group, a 1,4-cyclohexylene group, a 1,5-cycloheptylene group, a 1,5-cyclooctylene group, a 1,5-cyclononylene group and a 1,6-cyclodecylene group.

The specific examples of an epoxy monomer shown by the general formula [27] are, for example, epoxyalkanes such as ethylene oxide, 1,2-epoxypropane, 1,2-epoxybutane, 0,2,3-epoxybutane, 1,2-epoxypentane, 2,3-epoxypentane, 1,2-epoxyhexane, 1,2-epoxyheptane, 1,2-epoxyoctane, 1,2-epoxynonane, 1,2-epoxydecane, 1,2-epoxyundecane, 1,2-epoxydodecane, 1,2-epoxytridecane, 1,2-epoxytetradecane, 1,2-epoxyhexadecane, 1,2-epoxyheptadecane and 1,2-epoxyoctadecane; epoxyhaloalkanes such as 2,3-epoxy-1,1,1-trifluoropropane and 2,3-epoxy-1-chloropropane; epoxyalcohols such as 2,3-epoxypropanol; alkyl glycidyl ethers such as methyl glycidyl ether, ethyl glycidyl ether, propyl glycidyl ether, buthyl glycidyl ether, pentyl glycidyl ether, hexyl glycidyl ether, heptyl glycidyl ether, octyl glycidyl ether, nonyl glycidyl ether, decyl glycidyl ether, undecyl glycidyl ether and dodecyl glycidyl ether; aryl glycidyl ethers such as phenyl glycidyl ether and naphthyl glycidyl ether; alkenyl glycidyl ethers such as allyl glycidyl ether; glycidyl esters such as glycidyl methacrylate; 2,3-epoxyethylbenzene, α,α'-epoxybibenzyl, 2,3-epoxy-2,3-dihydro-1,4-naphthoquinone, epoxysuccinic acid, ethyl 2,3-epoxy-3-phenylbutyrate, 1,2,3,4-diepoxybutane and 1,2-epoxy-5-(epoxyethyl)cyclohexane.

The specific examples of the epoxy monomer shown by the general formula [29] are, for example, bis(3,4-epoxycyclohexyl) adipate and 3,4-epoxycyclohexyl-3,4-epoxycyclohexane carboxylic acid.

The specific examples of the vinyl ether monomer shown by the general formula [31] are, for example, alkyl vinyl ethers such as methyl vinyl ether, ethyl vinyl ether, propyl vinyl ether, isobutyl vinyl ether, 2-ethylhexyl vinyl ether, octadecyl vinyl ether, dodecyl vinyl ether and cyclohexyl vinyl ether; hydroxyalkyl vinyl ethers such as hydroxyethyl vinyl ether, hydroxybutyl vinyl ether, di(ethyleneglycol) monovinyl ether and 1,4-cyclohexanedimethanol monovinyl ether; divinyl ethers such as 1,4-butanediol divinyl ether, 1,6-hexanediol divinyl ether, 1,4-cyclohexanedimethanol divinyl ether, di(ethyleneglycol)divinyl ether, tri(ethyleneglycol)divinyl ether, di(proyleneglycol)divinyl ether and tri(proyleneglycol)divinyl ether; and propylene carbonate propenyl ether.

These may be used alone or in a suitable combination of two or more kinds thereof.

The above-mentioned polymerization method includes, for example, a solution polymerization, a bulk polymerization, a suspension polymerization and an emulsion polymerization.

The solvent for polymerization includes, for example, halogenated hydrocarbons such as chloroform, methylene chloride and 1,2-dichloroethane, hydrocarbons such as toluene, benzene and xylene; N,N-dimethylformamide and dimethylsulfoxide.

These solvents may be used alone or in a suitable combination of two or more kinds thereof.

The polymerization is preferably carried out under an inert gas atmosphere. The inert gas includes, for example, nitrogen gas and argon gas.

As amount of the onium salt of the present invention to be used, shown by the general formula [8] or [37] depends on kinds of monomer to be used and generally 0.1 to 200 wt %, preferably 1 to 50 wt % relative to various monomers.

A concentration of the monomer in the polymerization depends on kindes of monomer to be used and generally 1 to 100 wt % (no solvent), preferably 10 to 80 wt %. A polymerization temperature is generally −78 to 120° C., preferably −20 to 50° C.

A polymerization time depends reaction conditions such as a reaction temperature, kinds of an onium salt of the present invention and various monomers to be reacted or concentrations thereof, and generally 1 to 50 hours.

Post-treatment after the reaction may be performed in accordance with common methods generally performed in this field.

<2> Secondly, use of the onium salt of the present invention as an acid generator for a chemically amplified resist composition will be explained.

The preferable sulfonium salt of the present invention used as an acid generator includes is, for example, one shown by the general formula [9]:

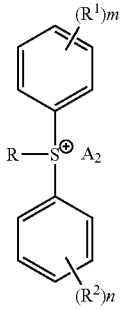

[9]

(wherein $A_2$ is an anion derived from an inorganic strong acid, an organic acid or a compound shown by the above-mentioned general formula [4]; and R, $R^1$, $R^2$, m and n have the same meaning as above), (among sulfonium salts shown by the general formula [1], corresponding to one wherein an anion shown by A is derived from an inorganic strong acid, an organic acid or a compound shown by the above-mentioned general formula [4]).

The iodonium salt of the present invention used as an acid generator includes such one as shown by the general formula [38]:

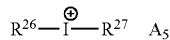

[38]

(wherein $A_5$ is an anion derived from an inorganic strong acid, an organic acid or a compound shown by the above-mentioned general formula [4]; and $R^{26}$, $R^{27}$ and others meanings have the same as described above.)

The onium salts of the present invention, shown by the general formulae [9] and [38] can be used alone as an acid generator, and more exellent effect can be expected by use of the salt in a combination with other acid generators. In particular, the onium salt of the present invention provides very superior effect as an acid generator when the salt is used in combination with an acid generator generating a weak acid such as a diazodisulfone compound having an alkyl group as a pending group.

The diazodisulfone compound to be used in combination includes, for example, one shown by the general formula [30]:

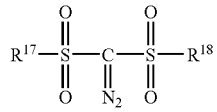

[30]

(wherein $R^{17}$ and $R^{18}$ are each independently an alkyl group.)

In the general formula [30], the alkyl group shown by $R^{17}$ may be straight chained, branched or cyclic, and includes one having generally 1 to 8, preferably 3 to 8 carbon atoms, and among others, preferably a branched or cyclic one, which is specifically exemplified by a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a 3-methylpentyl group, a 2-methylpentyl group, a 1,2-dimethylbutyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a cyclopropyl group, a cyclobutyl group, a cyclopentyl group, a cyclohexyl group, a cycloheptyl group and a cyclooctyl group.

The alkyl group shown by $R^{18}$ may be straight chained, branched or cyclic, and includes one having generally 3 to 8 carbon atoms, and among others, preferably a branched or cyclic one, which is specifically exemplified by an isopropyl group, an isobutyl group, a sec-butyl group, a tert-butyl group, an isopentyl group, a sec-pentyl group, a tert-pentyl group, a neopentyl group, an isohexyl group, a sec-hexyl group, a tert-hexyl group, a neohexyl group, a 3-methylpentyl group, a 2-methylpentyl group, a 1,2-dimethylbutyl group, an isoheptyl group, a sec-heptyl group, a tert-heptyl group, a neoheptyl group, an isooctyl group, a sec-octyl group, a tert-octyl group, a neooctyl group, a cyclopropyl group, a cyclobutyl group, a cyclopentyl group, a cyclohexyl group, a cycloheptyl group and a cyclooctyl group.

The specific examples of the diazodisulfone compound shown by the general formula [30] are, for example, bis(1-methylethylsulfonyl)diazomethane, bis(1,1-dimethylethylsulfonyl)diazomethane, bis(cyclohexylsulfonyl)diazomethane, methylsulfonyl-1-methylethylsulfonyldiazomethane, methylsulfonyl-1,1-dimethylethylsulfonyldiazomethane, methylsulfonylcyclohexylsulfonyldiazomethane, ethylsulfonyl-1-methylethylsulfonyldiazomethane, ethylsulfonyl-1,1-dimethylethylsulfonyldiazomethane, ethylsulfonylcyclohexylsulfonyldiazomethane, bis(octanesulfonyl)diazomethane, methylethylsulfonyl-1,1-dimethylethylsulfonyldiazomethane, 1-methylethylsulfonylcyclohexylsulfonyldiazomethane and 1,1-dimethylethylsulfonylcyclohexylsulfonyldiazomethane.

An amount of the onium salt of the present invention to be used, shown by the general formulae [9] and [38] is, when used alone, generally 0.1 to 10 wt %, preferably 0.5 to 5 wt %, relative to the resin amount of a chemically amplified resist composition, and when used together with other kind of acid generators, 0.05 to 5 wt %, preferably 0.1 to 3 wt % relative to the resin amount, while an amount of other kind of acid generators is generally 1 to 10 wt %, preferably 3 to 7 wt % relative to the resin amount.

The onium salt of the present invention, shown by the general formulae [9] and [38], can generate an acid by irradiation with light from a high pressure mercury lamp and a metal halide lamp, deep UV rays, KrF excimer laser, ArF excimer laser, $F_2$ excimer laser (157 nm), electron beams (EB) and soft X-rays. Therefore, the onium salt of the present invention, shown by the general formulae [9] and [38] is useful as an acid generator for a resist by irradiation with light from high pressure mercury lamp and metal halide lamp, deep UV rays, KrF excimer laser, ArF excimer laser, $F_2$ excimer laser (157 nm), electron beams and soft X-rays, in particular, light from a high pressure mercury lamp and a metal halide lamp.

Since the onium salt of the present invention, shown by the general formulae [8], [9], [37] and [38] has a heterocycle in the cation moiety, it provides higher absorption wavelength region than conventional onium salts and provides an improved acid generation efficiency by irradiation with, for example, light from a high pressure mercury lamp or a metal halide lamp, UV rays, far ultraviolet ray, KrF excimer laser, ArF excimer laser, $F_2$ excimer laser, electron beams, X-rays and radiactive rays. In particular, since these compounds have absorption wavelength, at wavelength region of light, for example, from a high pressure mercury lamp and a metal halide lamp, use of these as light source can generate an acid effectively without the addition of a conventional sensitizer.

The onium salt of the present invention has little absorption in wavelength region not shorter than 400 nm, which provides good transparency in the visible light region. Therefore, use of these as a cationic photopolymerization initiator for such as coating materials, adhesives and paints provides good effect of remaining nearly uneffected by transparency of a obtained polymer.

Further, among iodonium salts of the present invention, shown by the general formulae [37] and [38], one having two heterocycles in the cation moiety has improved light absorption efficiency, when a high pressure mercury lamp or a metal halide lamp is used as light source, therefore use of these as light source can provide higher acid generation efficiency.

The onium salt of the present invention, shown by the general formulae [8], [9], [37] and [38] can form a polymer with high hardness even when $PF_6^-$ is used as a counter anion without having such a problem that conventional sulfonium salts and iodonium salts, wherein a counter anion thereof is $PF_6^-$, photocuring is significantly lowered.

On the other hand, 2-(phenyliodonium)xanthene-9-one tetrafluoroborate ($BF_4^-$), as an analogous compound of the present invention, is an iodonium salt having one heterocycle at the cation moiety, however, one having as an anion $BF_4^-$, which is derived from a weak acid among an inorganic strong acid, therefore, is has drawbacks that acid generation efficiency is low and use of a sensitizer is required, when a high pressure mercury lamp or a metal halide lamp is used as light source.

Therefore, use of an onium salt shown by the above-mentioned general formulae [8] and [37] as a cationic photopolymerization initiator can form a polymer with good transparency and high hardness, on the other hand, use of an onium salt shown by the above-mentioned general formulae [9] and [38] as an acid generator for a resist can provide a resist composition with high sensitivity.

In the following, the present invention is explained in further detail referring to examples, but the present invention is not limited thereto by any means.

EXAMPLE

Example 1

Synthesis of diphenyl(coumarin-7-yl)sulfonium trifluoromethanesulfonate

To 160 ml of dichloromethane were dissolved 20.2 g (0.1 mol) of diphenylsulfoxide and 17.5 g (0.12 mol) of coumarin, and 28.2 g (0.1 mol) of trifluoromethanesulfonic anhydride was added dropwise thereto at −70 to −60° C., followed by gradually warming to room temperature and reacting with stirring for 2 hours. After completion of the reaction, the obtained reaction solution was washed with water (160 ml×5 times) and concentrated under reduced pressure, followed by purifying the resulting crude product by a column chromatography to obtain 32.1 g of objective substance as pale yellow glassy substance (yield: 67%).

$^1$H NMR (CDCl$_3$) δppm: 6.53(1H, d, Ar—H), 7.55(1H, d, Ar—H), 7.71-7.79(11H, m, Ar—H), 8.02(1H, d, Ar—H), 8.49(1H, s, Ar—H)

Example 2

Synthesis of diphenyl(coumarin-7-yl)sulfonium hexafluorophosphate

To 200 ml of dichloromethane was dissolved 24.0 g (0.05 mol) of (coumarin-7-yl)diphenylsulfonium trifluoromethanesulfonate obtained in Example 1, and 18.4 g (0.1 mol) of potassium hexafluorophosphate and 200 ml of water was added thereto, followed by stirring at room temperature for 2 hours. Then, the solution was fractionated and 9.2 g (0.05 mol) of potassium hexafluorophosphate and 100 ml of water were further added to the obtained dichloromethane layer, followed by stirring at room temperature for 2 hours, and then fractionating the solution. The obtained dichloromethane layer was washed with 200 ml of water and concentrated to dryness under reduced pressure to obtain 23.8 g of objective substance as pale yellow glassy substance (yield: 98%).

$^1$H NMR (CDCl$_3$) δppm: 6.63(1H, d, Ar—H), 7.55(1H, d, Ar—H), 7.69-7.82(11H, m, Ar—H), 7.92(1H, d, Ar—H), 8.19(1H, s, Ar—H)

Example 3

Synthesis of diphenyl(xanthene-9-one-2-yl)sulfonium trifluoromethanesulfonate

To 320 ml of dichloromethane were dissolved 20.2 g (0.1 mol) of diphenylsulfoxide and 19.6 g (0.1 mol) of xanthene-9-one, and 28.2 g (0.1 mol) of trifluoromethanesulfonic anhydride was added dropwise thereto at −70 to −60° C., followed by gradually warming to room temperature and reacting with stirring for 4 hours. After completion of the reaction, the obtained reaction solution was washed with water (160 ml×4 times) and concentrated under reduced pressure, followed by purifying the obtained crude product with column chromatography to obtain 30.7 g of objective substance as pale brown glassy substance (yield: 58%).

$^1$H NMR (CDCl$_3$) δppm: 7.49(1H, t, Ar—H), 7.60(1H, d, Ar—H), 7.72-7.86(11H, m, Ar—H), 7.94(1H, d, Ar—H), 8.25(1H, t, Ar—H), 8.48(1H, d, Ar—H)

Example 4

Synthesis of diphenyl(xanthene-9-one-2-yl)sulfonium hexafluorophosphate

The same procedure as in Example 2 was conducted, except for using 26.5 g (0.05 mol) of diphenyl(xanthene-9-one-2-yl)sulfonium trifluoromethanesulfonate instead of diphenyl(coumarin-6-yl)sulfonium trifluoromethanesulfonate used in Example 2 to obtain 24.6 g objective substance as pale brown glassy substance (yield: 94%).

$^1$H NMR (CDCl$_3$) δppm: 7.27(1H, t, Ar—H), 7.59(1H, d, Ar—H), 7.72-7.89(11H, m, Ar—H), 7.94(1H, d, Ar—H), 8.25(1H, t, Ar—H), 8.48(1H, d, Ar—H)

Example 5

Synthesis of bis(coumarin-7-yl)iodonium hexafluorophosphate

To 50 ml of acetic anhydride was dissolved 14.6 g (0.1 mol) of coumarin, and 10.7 g (0.05 mol) of potassium iodate was added thereto at 0° C., and then mixed acid consisting of 25 g (0.25 mol) of concentrated sulfuric acid and 30 g of acetic anhydride was added dropwise thereto at 0 to 7° C. for 2 hours, followed by gradually warming to room temperature and reacting with stirring for 5 hours. After completion of the reaction, the reaction solution was poured in 200 ml of ice water, and 18.4 g (0.1 mol) of potassium hexafluorophosphate was added thereto and 100 ml of dichloromethane was poured thereinto, followed by stirring at room temperature for 2 hours. The precipitated crude crystal was filtered off to obtain 8.0 g of pale yellow crystal. The obtained crystal was dissolved in 60 ml of acetone and then 100 ml of ethyl acetate was gradually poured thereto, followed by filtering the precipitated crystal and drying under vacuum at 50° C. for 2 hours to obtain 6.5 g of objective substance as pale yellow crystal (yield: 23%).

m.p.: 227-228° C. (decomposition) $^1$H NMR (CDCl$_3$) δppm: 6.64 (2H, d, Ar—H), 7.56 (2H, d, Ar—H), 8.06 (2H, d, Ar—H), 8.42(2H, d, Ar—H), 8.61(2H, s, Ar—H)

Example 6

Synthesis of bis(xanthene-9-one-2-yl)iodonium hexafluorophosphate

To 100 ml of acetic anhydride was suspended 19.6 g (0.1 mol) of xanthene-9-one, and 10.7 g (0.05 mol) of potassium iodate was added thereto at 0° C., and then mixed acid consisting of 25 g (0.25 mol) of concentrated sulfuric acid and 30 g of acetic anhydride was added dropwise thereto at 0 to 7° C. over 2 hours, followed by gradually warming to room temperature and reacting with stirring for 6 hours. After completion of the reaction, the reaction solution was poured in 200 ml of ice water, and 100 ml of dichloromethane was added thereto to dissolve insolble substance. Then 18.4 g (0.1 mol) of potassium hexafluorophosphate was added and stirred thereto at room temperature for 2 hours, followed by filtering precipitated crystal off to obtain 8.0 g of yellowish pale brown crystal. The obtained crystal was dissolved in 100 ml of acetone and then 100 ml of ethyl acetate was gradually poured thereto to precipitate crystal, followed by filtering precipitated crystal off and drying under vacuum at 50° C. for 2 hours to obtain 6.6 g of objective substance as yellowish pale brown crystal (yield: 20%).

m.p.: 223° C. (decomposition) $^1$HNMR (CDCl$_3$) δppm: 7.53(2H, t, Ar—H), 7.69(2H, d, Ar—H), 7.85-7.94(4H, m, Ar—H), 8.20(2H, d, Ar—H), 8.75(2H, d, Ar—H), 9.23(2H, s, Ar—H)

Example 7

Synthesis of 7-(phenyliodonio)coumarin hexafluorophosphate

To 80 ml of acetic anhydride was suspended 7.3 g (0.05 mol) of coumarin and 16.1 g (0.05 mol) of iodobenzene diacetate, and 10 g (0.1 mol) of concentrated sulfuric acid was added dropwise thereto at 0 to 7° C. for 1 hour, followed by gradually warming to room temperature and reacting with stirring for 8 hours. After completion of the reaction, the reaction solution was poured in 200 ml of ice water, and 150 ml of dichloromethane was added thereto to dissolve insolble substance. Then 18.4 g (0.1 mol) of potassium hexafluorophosphate was added to the obtained solution, followed by stirring at room temperature for 2 hours. The dichloromethane layer obtained by fractionation was washed with 100 ml of water twice. The obtained dichloromethane layer was semi concentrated under reduced pressure and the precipitated crystal was filtered off, followed by drying under vacuum at 50° C. for 2 hours to obtain 2.4 g of objective substance as pale yellow crystal (yield: 10%).

m.p.: 211° C. (decomposition) $^1$H NMR (CDCl$_3$) δppm: 6.64(1H, d, Ar—H), 7.57(3H, t, Ar—H), 7.68(1H, t, Ar—H), 8.05(1H, d, Ar—H), 8.25(2H, d, Ar—H), 8.41(1H, d, Ar—H), 8.63(1H, s, Ar—H)

Example 8

Synthesis of 2-(phenyliodonio)xanthene-2-one hexafluorophosphate

To 80 ml of acetic anhydride were suspended 9.8 g (0.05 mol) of xanthene-9-one and 16.1 g (0.05 mol) of iodobenzene diacetate, and 10 g (0.1 mol) of concentrated sulfuric acid was added dropwise thereto at 0 to 7° C. for 1 hour, followed by gradually warming to room temperature and reacting with stirring for 8 hours. After completion of the reaction, the reaction solution was poured in 200 ml of ice water, and 150 ml of toluene was added thereto to dissolve insoluble substance and fractionation. Then 18.4 g (0.1 mol) of potassium hexafluorophosphate was added to water layer and stirred at room temperature for 2 hours. The precipitated crystal was filtered off, followed by drying under vacuum at 50° C. for 2 hours to obtain 16.1 g of objective substance as pale yellow crystal (yield: 59%).

m.p.: 222° C. (decomposition) $^1$HNMR (CDCl$_3$) δppm: 7.51-7.58(3H, m, Ar—H), 7.69(2H, t, Ar—H), 7.83(1H, d, Ar—H), 7.93(1H, t, Ar—H), 8.20(1H, d, Ar—H), 8.36(2H, d, Ar—H), 8.62(1H, d, Ar—H), 9.05(1H, s, Ar—H)

Comparative Example 1

Synthesis of diphenyl(thioxanthene-9-one-2-yl)sulfonium trifluoromethanesulfonate To 320 ml of dichloromethane were suspended 20.2 g (0.1 mol) of diphenylsulfoxide and 21.2 g (0.1 mol) of thioxanthene-9-one, and 28.2 g (0.1 mol) of trifluoromethanesulfonic anhydride was added dropwise thereto at −70 to −60° C., followed by gradually warming to room-temperature and reacting with stirring for 3 hours. After completion of the reaction, the obtained reaction solution was washed with water (320 ml×5 times) and the obtained dichloromethane layer was concentrated to dryness under reduced pressure. The obtained crude product was purified by column chromatography to obtain 18.6 g of objective substance as yellow glassy substance (yield: 34%).

$^1$H NMR (CDCl$_3$) δppm: 7.40-7.83(11H, m, Ar—H), 7.93(1H, q, Ar—H), 8.02(1H, d, Ar—H), 8.27(1H, q, Ar—H), 8.54(1H, d, Ar—H), 8.60(1H, d, Ar—H), 8.68(1H, s, Ar—H)

Comparative Example 2

Synthesis of diphenyl(thioxanthene-9-one-2-yl)sulfonium hexafluorophosphate

The same procedure as in Example 2 was conducted, except for using 13.7 g (0.025 mol) of diphenyl(thioxanthene-9-one-2-yl)sulfonium trifluoromethanesulfonate instead of diphenyl(coumarin-6-yl)sulfonium trifluoromethanesulfonate used in Example 2 to obtain 13.0 g of objective substance as yellow glassy substance (yield: 96%).

$^1$H NMR (CDCl$_3$) δppm: 7.45-7.85(11H, m, Ar—H), 7.96(1H, q, Ar—H), 7.98(1H, d, Ar—H), 8.08(1H, q, Ar—H), 8.52(1H, d, Ar—H), 8.60(1H, d, Ar—H), 8.73(1H, s, Ar—H)

Comparative Example 3

Synthesis of diphenyl(7-chlorothioxanthene-9-one-2-yl)sulfonium hexafluorophosphate To 320 ml of dichloromethane were suspended 20.2 g (0.1 mol) of diphenylsulfoxide and 24.6 g (0.1 mol) of 2-chlorothioxanthene-9-one, and 28.2 g (0.1 mol) of trifluoromethanesulfonic anhydride was added dropwise thereto at −70 to −60° C., followed by gradually warming to room temperature and reacting with stirring for 3 hours. After completion of the reaction, the obtained reaction solution was washed with water (320 ml×5 times) and 18.4 g (0.1 mol) of potassium hexafluorophosphate and 200 ml of water were added to the obtained dichloromethane layer, followed by stirring at room temperature for 2 hours and fractionating the solution. Then, 9.2 g (0.05 mol) of potassium hexafluorophosphate and 100 ml of water were further added to the obtained dichloromethane layer, followed by stirring at room temperature for 2 hours and fractionating the solution. Then the obtained dichloromethane layer was washed with 200 ml of water and concentrated to dryness under reduced pressure. The obtained crude product was purified by column chromatography to obtain 4.0 g of objective substance as pale yellow glassy substance (yield: 7%).

$^1$H NMR (CDCl$_3$) δppm: 7.79-7.95(11H, m, Ar—H), 8.05(1H, d, Ar—H), 8.14(1H, d, Ar—H), 8.31(1H, d, Ar—H), 8.37(1H, s, Ar—H), 8.73(1H, s, Ar—H)

Comparative Example 4

Synthesis of diphenyl(5,7-diethylthioxanthene-9-one-2-yl)sulfonium trifluoromethanesulfonate To 320 ml of dichloromethane were dissolved 20.2 g (0.1 mol) of diphenylsulfoxide and 26.8 g (0.1 mol) of 2,4-diethylthioxanthene-9-one, and 28.2 g (0.1 mol) of trifluoromethanesulfonic anhydride was added dropwise thereto at −70 to −60° C., followed by gradually warming to room temperature and reacting with stirring for 4 hours. After completion of the reaction, the obtained reaction solution was washed with water (160 ml×4 times) and concentrated under reduced pressure. The obtained crude product was purified by column chromatography to obtain 38.6 g of objective substance as yellow glassy substance (yield: 64%).

$^1$HNMR (CDCl$_3$) δppm: 1.28(3H, t, CH$_3$), 1.38(3H, t, CH$_3$), 2.80(2H, q, CH$_2$), 2.93(2H, q, CH$_2$), 7.46(1H, s, Ar—H), 7.70-7.85(11H, m, Ar—H), 8.07(1H, w, Ar—H), 8.28(1H, s, Ar—H), 8.66(1H, s, Ar—H)

Comparative Example 5

Synthesis of diphenyl(5,7-diethylthioxanthene-9-one-2-yl)sulfonium hexafluorophosphate The same procedure as in Example 2 was conducted, except for using 30.1 g (0.05 mol) of diphenyl(5,7-diethylthioxanthene-9-one-2-yl)sulfonium trifluoromethanesulfonate instead of diphenyl(coumarin-6-yl)sulfonium trifluoromethanesulfonate used in Example 2 to obtain 29.0 g of objective substance as yellow glassy substance (yield: 97%).

$^1$H NMR (CDCl$_3$) δppm: 1.32(3H, t, CH$_3$), 1.36(3H, t, CH$_3$), 2.77(2H, q, CH$_2$), 2.91(2H, q, CH$_2$), 7.46(1H, s, Ar—H), 7.72-7.85(11H, m, Ar—H), 8.05(1H, w, Ar—H), 8.28(1H, s, Ar—H), 8.71(1H, s, Ar—H)

Comparative Example 6

Synthesis of 2-(phenyliodonio)xanthene-9-one tetrafluoroborate

To 80 ml of acetic anhydride were suspended 9.8 g (0.05 mol) of xanthene-9-one and 16.1 g (0.05 mol) of iodobenzene diacetate, and 10 g (0.1 mol) of concentrated sulfuric acid was added dropwise thereto at 0 to 7° C. for 1 hour, followed by gradually warming to room temperature and reacting with stirring for 8 hours. After completion of the reaction, the obtained reaction solution was poured into 200 ml of ice water, and 150 ml of toluene was added thereto to dissolve insoluble substance. The solution was fractionated and 12.6 g (0.1 mol) of potassium tetrafluoroborate was added to the obtained water layer, followed by stirring at room temperature for 2 hours. The precipitated crystal was filtered off and dried at 50° C. under vacuum for 2 hours to obtain 11.4 g of 2-(phenyliodonio)xanthene-9-one tetrafluoroborate as pale orange crystal (yield: 47%).

m.p.: 229-231° C. (decomposition) $^1$H NMR (CDCl$_3$) δppm: 7.51-7.56(3H, Q, Ar—H), 7.66-7.73(2H, m, Ar—H), 7.83(1H, d, Ar—H), 7.93(1H, t, Ar—H), 8.20(1H, d, Ar—H), 8.36(2H, d, Ar—H), 8.62(1H, d, Ar—H), 9.06(1H, s, Ar—H)

Example 9

Measurement of UV-Visible Ray Absorption Spectra 0.0016 (w/v) % acetonitrile solution of compounds obtained in Examples 1 to 8 and Comparative Examples 1 to 6 (about $3 \times 10^{-5}$ mol/l) were prepared to measure ultraviolet-visible ray absorption spectra. As reference examples, absorption spectra of triphenylsulfonium hexafluorophosphate (Reference Example 1) and diphenyliodonium hexafluorophosphate (Reference Example 2) were also measured. Table 1 shows wavelength (nm) for maximum absorption, molecular extinction coefficient (ε) at said wavelength and molecular extinction coefficient (ε) at 300 nm, 350 nm and 400 nm. Absorption curve data on sulfonium salts are shown in FIGS. 1 and 2 and the data on iodonium salts are shown in FIG. 3, respectively.

Figure 1:
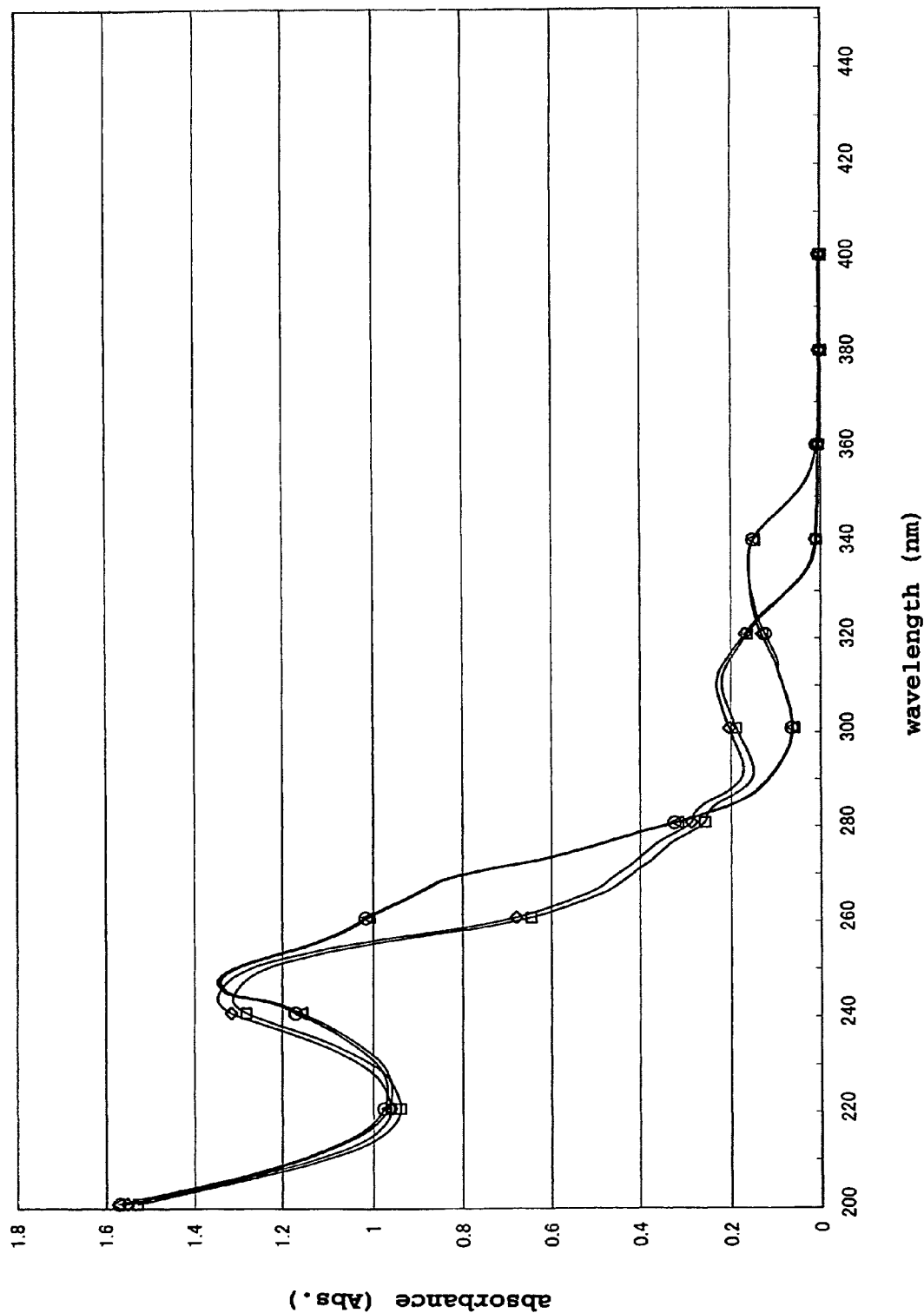
FIG. 1 shows UV-visible ray absorption spectra curves data on Examples 1 to 4.

Each curve code in FIG. 1 shows the following compounds, respectively:
- –□– curve: a sulfonium salt of the present invention (Example 1)
- –◇– curve: a sulfonium salt of the present invention (Example 2)
- –△– curve: a sulfonium salt of the present invention (Example 3)
- –○– curve: a sulfonium salt of the present invention (Example 4)

Each curve code in FIG. 2 shows the following compound, respectively:
- –◇– curve: a compound of Comparative Example 1
- –△– curve: a compound of Comparative Example 2
- –□– curve: a compound of Comparative Example 3
- ··×·· curve: a compound of Comparative Example 4
- ··○·· curve: a compound of Comparative Example 5
- –+– curve: a compound of Reference Example 1

Each curve code in FIG. 3 shows the following compound, respectively:
- –□– curve: an iodonium salt of the present invention (Example 5)
- –◇– curve: an iodonium salt of the present invention (Example 6)
- –△– curve: an iodonium salt of the present invention (Example 7)
- –○– curve: an iodonium salt of the present invention (Example 8)
- –×– curve: a compound of Comparative Example 6
- –+– curve: a compound of Reference Example 2

As is clear from the results in FIGS. 1 and 2, triphenylsulfonium hexafluorophosphate (Reference Example 1), as a conventional sulfonium salt, has little absorption in wavelength region not shorter than 300 nm and sulfonium salts having thioxantone skeleton, wherein the anion thereof is hexafluorophosphate (Comparative Examples 1 to 5) have absorption in wavelength region not shorter than 400 nm and thus provides yellow color. Therefore, when the polymerization of monomer is conducted by using them as cationic photopolymerization initiators for light source of a high pressure mercury lamp having effective wavelength not shorter than UV region (300 nm and longer), use of triphenylsulfonium hexafluorophosphate (Reference Example 1) provides a problem of poor acid generation efficiency, and further use of sulfonium salts having thioxantone skeleton (Comparative Examples 1 to 5) provides good acid generation efficiency, but a problem that because said sulfonium salts themselves shows yellow color in visible region, the obtained polymers give rellow color and therefore they have lower transparency.

On the other hand, sulfonium salts of the present invention, have absorption at 300 to 360 nm region and no absorption at not shorter than 400 nm, and thus it was found that when they are used as cationic photopolymerization initiators for light source of a high pressure mercury lamp to polymerize a monomer, they provide good acid generation efficiency, and the obtained polymers have good transparency in the visible light region.

As is clear from the results in FIG. 3, diphenyliodonium hexafluorophosphate, as a conventional iodonium salt, has

TABLE 1

| Cationic photopolymerization initiator | Maximum absorption wave length (nm) (Molecular extinction coefficient) | | Molecular extinction coefficient | | |
|---|---|---|---|---|---|
| | | | 300 nm | 350 nm | 400 nm |
| Compd. of Example 1 | 243 (39380) | 310 (6593) | 5634 | 174 | 0 |
| Compd. of Example 2 | 243 (40130) | 310 (6864) | 6063 | 229 | 0 |
| Compd. of Example 3 | 248 (44410) | 335 (5260) | 1646 | 32 | 0 |
| Compd. of Example 4 | 248 (44290) | 336 (5270) | 2127 | 31 | 0 |
| Compd. of Comparative Example 1 | 315 (16010) | 371 (2773) | 12210 | 2524 | 592 |
| Compd. of Comparative Example 2 | 315 (15820) | 378 (2688) | 12000 | 2444 | 519 |
| Compd. of Comparative Example 3 | 321 (19070) | 387 (4464) | 8689 | 3136 | 2251 |
| Compd. of Comparative Example 4 | 324 (16000) | 379 (3731) | 12750 | 4623 | 2564 |
| Compd. of Comparative Example 5 | 324 (15890) | 379 (3731) | 12680 | 4560 | 2522 |
| Compd. of Example 10 | 248 (42240) | 310 (13420) | 11730 | 382 | 32 |
| Compd. of Example 11 | 252 (54540) | 335 (9246) | 6332 | 3302 | 39 |
| Compd. of Example 12 | 241 (31370) | 309 (6376) | 5512 | 0 | 0 |
| Compd. of Example 13 | 248 (41130) | 337 (5347) | 2198 | 1411 | 0 |
| Compd. of Comparative Example 6 | 248 (41130) | 337 (5347) | 2890 | 1821 | 0 |
| triphenylsulfonium hexafluorophosphate | 197 (59090) | 233 (18220) | 175 | 50 | 0 |
| diphenyliodonium hexafluorophosphate | 194 (35600) | 229 (14400) | 207 | 0 | 0 | little absorption in wavelength region not shorter than 300 nm, while iodonium salts of the present invention have absorption in wavelength region not shorter than 300 nm and little absorption in wavelength region not shorter than 400 nm, and there it was found that iodonium salts of the present invention, just like sulfonium salts of the present invention, have acid generation efficiency when they are used as cationic photopolymerization initiators for light source of a high pressure mercury lamp to polymerize a monomer, and the obtained polymers have high transparency in the visible light region.

Example 10

Photocuring Test

A mixture was prepared by mixing 7 g of 3,4-epoxycyclohexylmethyl-3,4-epoxycyclohexanecarboxylate, 3 g of cyclohexeneoxide and 0.20 g of a 50% (w/w) propylene carbonate solution of each compound obtained in Examples 2 to 4 as a cationic photopolymerization initiator. This solution was coated on a glass plate to obtain film with thickness of 40±10 μm, followed by irradiation with a 50 W/cm high pressure mercury lamp for 60 seconds. Pencil hardness was measured just after the irradiation and one day after the irradiation. As comparative examples, a photocuring test of triphenylsulfonium hexafluorophosphate was also performed at the same time. The results are shown in Table 2.

TABLE 2

| Cationic photopolymerization initiator | Just after | One day after |
|---|---|---|
| Compound of Example 2 | HB | H |
| Compound of Example 5 | HB | H |
| Compound of Example 6 | 4H | 4H |
| Compound of Example 8 | HB | H |
| Compound of Comparative Example 1 | HB | H |
| Compound of Comparative Example 2 | 4H | 4H |
| Compound of Comparative Example 5 | HB | H |
| Compound of Comparative Example 6 | 2B | B |
| triphenylsulfonium hexafluorophosphate | HB | HB |
| diphenyliodonium hexafluorophosphate | HB | HB |

As is clear from the results of the comparison of a sulfonium salt in Example 2 with triphenylsulfonium hexafluorophosphate, and comparison of idonium salts in Examples 5, 6 and 8 with diphenyliodonium hexafluorophosphate, in Table 2, it was found that hardness, of sulfonium salts and iodonium salts of the present invention, just after curing provides equivalent to or higher than those of conventional sulfonium salts and iodonium salts, and higher hardness, of said salts of the present invention, one day after curing provides higher than those of conventional sulfonium salts and iodonium salts.

Further, it is also clear from the results of the comparison of sulfonium salts having thioxantone skeleton in Comparative Examples 1, 2 and 5 with a sulfonium salt of the present invention (Example 2) that, as is also described in discussion on Table 1, sulfonium salts having thioxantone skeleton have yellow color and are not preferable due to providing poor transparency to the obtained polymers when used as coating materials, adhesives and paints, although a compound in Comparative Example 2 provides hardness higher than that of a compound of the present invention.

Furthermore, as is clear from the results of the comparison between a compound ($PF_6^-$) in Example 8 and a compound ($BF_4^-$) in Comparative Example 6, is was found that iodonium salts of the present invention provide higher hardness than conventional iodonium salts from the viewpoint of the results of hardness just after and one day after curing. It was also clear from the comparison between the results in Examples 5 and 6 and Example 8, that among others, iodonium salts, one wherein both $R^{26}$ and $R^{27}$ in the general formula [35] are one shown by the general formula [2] or [3], can be used as a cationic initiator to obtain polymers with higher hardness.

Example 11

Photopolymerization Test

As cationic photo polymerization initiators, 20% (w/w) propylene carbonate solutions of compounds obtained in Examples 4 to 8 were prepared. They were each added and mixed to 50.00 g of cyclohexeneoxide to become the polymerization initiator concentration of 0.5% (w/w). To a test tube added 5 ml of this solution, followed by nitrogen bubbling and sealing the tube with parafilm (trade name). The reaction solution was kept to 17 to 22° C. in a water bath, followed by irradiation with a 100 W high pressure mercury lamp (HL-100 model: mfd. by Fuji Glass Co., Ltd.) from measurement distance of 7 cm for predetermined time to precipitate a polymer from excess of methanol solution. The obtained polymer was washed several times, followed by filtering with a glass filter and drying. Polymerization rate was calculated by dividing polymer weigh after drying by monomer weight at the time tube charged to the test tube.

The polymerization rate to each irradiation time is measured. The results are shown in FIG. 4.

Each curve code in FIG. 4 shows the following compound, respectively:

–□–curve: a compound of Example 4

–*–curve: a compound of Example 5

–◇–curve: a compound of Example 6

–○–curve: a compound of Example 8

••+•• curve: a compound of Comparative Example 2

••Δ•• curve: a compound of Comparative Example 3

As is clear from the results in FIG. 4, use of compounds in Examples 2, 4 to 6 as polymerization initiators provides polymerization rate quite similar to obtain by use of compounds in Comparative Examples 2 and 3 as polymerization initiators.

INDUSTRIAL APPLICABILITY

An onium salt of the present invention has a heterocycle in the cation moiety, and thus provides higher light absorption efficiency of light such as a high pressure mercury lamp, a metal halide lamp, UV rays, deep UV rays, KrF excimer laser, ArF excimer laser, $F_2$ excimer laser, electron beams, X-rays and radioactive rays, in particular, light such as a high pressure mercury lamp and a metal halide lamp. Therefore, onium salts shown by the general formulae [8], [9], [37] and [38] have advantage such as providing improved acid generation efficiency compared with conventional onium salts, when a high pressure mercury lamp or a metal halide lamp is used as light source among various light sources. Furthermore, an onium salt of the present invention has little absorption at wavelength not shorter than 400 nm, and thus provides effect that a polymer obtained by using said onium salts as a cationic photopolymerization initiator maintains transparency in the visible light region. Such use of said onium salt as an acid generator for a chemically amplified resist can prepare a resist composition with high sensitivity to light source of a high pressure mercury lamp and a metal halide lamp.

What is claimed is:

1. A heterocycle-containing onium salt shown by the general formula [1]:

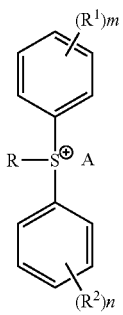

[wherein R is a group shown by the general formula [2]:

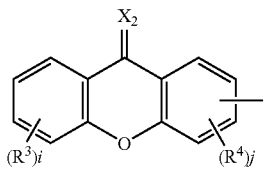

(wherein $R^3$ and $R^4$ are each independently a halogen atom, an alkyl group which may have a halogen atom or an aryl group as a substituent, or an aryl group which may have a halogen atom or an alkyl group having 1 to 6 carbon atoms as a substituent; $X_2$ is an oxygen atom or a sulfur atom; i is an integer of 0 to 4; and j is an integer of 0 to 3), or a group shown by the general formula [3]:

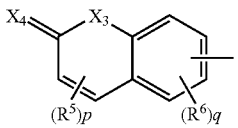

(wherein $R^5$ and $R^6$ are each independently a halogen atom, an alkyl group which may have a halogen atom or an aryl group as a substituent, or an aryl group which may have a halogen atom or an alkyl group having 1 to 6 carbon atoms as a substituent; $X_3$ and $X_4$ are each independently an oxygen atom or a sulfur atom; p is an integer of 0 to 2; and q is an integer of 0 to 3); $R^1$ and $R^2$ are each independently a halogen atom, an alkyl group which may have a halogen atom or an aryl group as a substituent, or an aryl group which may have a halogen atom or an alkyl group having 1 to 6 carbon atoms as a substituent; m and n are each independently an integer of 0 to 5; and A is a halogen atom or an anion derived from an inorganic strong acid, an organic acid or a compound shown by the general formula [4]:

$$HM_1(R^7)_4 \quad [4]$$

(wherein $M_1$ is a boron atom or a gallium atom; and $R^7$ is an aryl group which may have a substituent selected from a haloalkyl group having 1 to 6 carbon atoms, a halogen atom, a nitro group and a cyano group)].

2. A salt according to claim 1, wherein the anion derived from an inorganic strong acid, shown by A is one derived from nitric acid, sulfuric acid, halosulfuric acid, perhalogenic acid or a compound shown by the general formula [5]:

$$HM_2F_k \quad [5]$$

(wherein $M_2$ is a metalloid atom or a metal atom; and k is an integer of 4 or 6).

3. A salt according to claim 2, wherein the metalloid atom shown by $M_2$ is a boron atom, a silicon atom, a phosphorus atom, an arsenic atom or an antimony atom; and the metal atom shown by $M_2$ is an aluminum atom, a titanium atom, an iron atom, a nickel atom, a zirconium atom or a gallium atom.

4. A salt according to claim 1, wherein the anion derived from the organic acid shown by A is one derived from a sulfonic acid shown by the general formula [6]:

$$R^8{-}SO_3H \quad [6]$$

(wherein $R^8$ is an alkyl group, an aryl group or an aralkyl group, which may have a halogen atom), or a carboxylic acid shown by the general formula [7]:

$$R^9{-}COOH \quad [7]$$

(wherein $R^9$ is an alkyl group, an aryl group or an aralkyl group, which may have a halogen atom).

5. A salt according to claim 1, wherein R is a group shown by the general formula [2].

6. A salt according to claim 5, wherein $X_2$ in the general formula [2] is an oxygen atom.

7. A salt according to claim 5, wherein the group shown by the general formula [2] is a xanthonyl group.

8. A salt according to claim 1, wherein R is a group shown by the general formula [3].

9. A salt according to claim 8, wherein each $X_3$ and $X_4$ in the general formula [3] is an oxygen atom.

10. A salt according to claim 8, wherein the group shown by the general formula [3] is a coumarinyl group.

11. A salt according to claim 1, wherein the sulfonium salt shown by the general formula [1] is diphenyl(xanthene-9-one-2-yl)sulfonium hexafluorophosphate or (coumarin-7-yl)diphenylsulfonium hexafluorophosphate.

12. A cationic photopolymerization initiator comprising a heterocycle-containing onium salt shown by the general formula [8]:

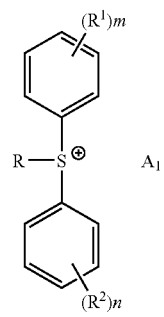

[wherein R is a group shown by the general formula [2]:

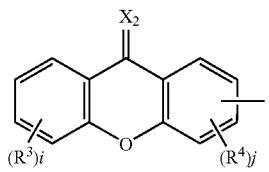

[2]

(wherein $R^3$ and $R^4$ are each independently a halogen atom, an alkyl group which may have a halogen atom or an aryl group as a substituent, or an aryl group which may have a halogen atom or an alkyl group having 1 to 6 carbon atoms as a substituent; $X_2$ is an oxygen atom or a sulfur atom; i is an integer of 0 to 4; and j is an integer of 0 to 3), or a group shown by the general formula [3]:

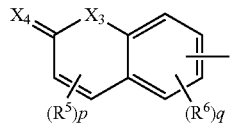

[3]

(wherein $R^5$ and $R^6$ are each independently a halogen atom, an alkyl group which may have a halogen atom or an aryl group as a substituent, or an aryl group which may have a halogen atom or an alkyl group having 1 to 6 carbon atoms as a substituent; $X_3$ and $X_4$ are each independently an oxygen atom or a sulfur atom; p is an integer of 0 to 2; and q is an integer of 0 to 3); $R^1$ and $R^2$ are each independently halogen atom, an alkyl group which may have a halogen atom or an aryl group as a substituent, or an aryl group which may have a halogen atom or an alkyl group having 1 to 6 carbon atoms as a substituent; m and n are each independently an integer of 0 to 5; and $A_1$ is an anion derived from an inorganic strong acid, a sulfonic acid or a compound shown by the general formula [4]:

[4]

(wherein $M_1$ is a boron atom or a gallium atom; $R^7$ is an aryl group which may have a substituent selected from a haloalkyl group having 1 to 6 carbon atoms, a halogen atom, a nitro group and a cyano group)].

13. A polymerization initiator according to claim 12, wherein $A_1$ is an anion derived from the compound shown by the general formula [4] or an inorganic strong acid shown by the general formula [5]:

[5]

(wherein $M_2$ is a metalloid atom or a metal atom; and k is an integer of 4 or 6).

14. A polymerization initiator according to claim 12, wherein the sulfonium salt shown by the general formula [8] is diphenyl(xanthene-9-one-2-yl)sulfonium hexafluorophosphate or (coumarin-7-yl)diphenylsulfonium hexafluorophosphate.

15. A method for polymerization of an epoxy monomer, which comprises using the polymerization initiator in claim 12.

16. A method for polymerization of a vinyl ether monomer, which comprises using the polymerization initiator in claim 12.

17. An acid generator for a resist, comprising a sulfonium salt shown by the general formula [9]:

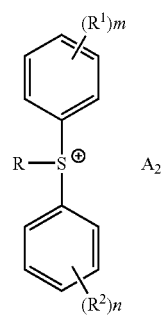

[9]

[wherein R is a group shown by the general formula [2]:

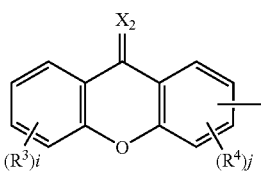

[2]

(wherein $R^3$ and $R^4$ are each independently a halogen atom, an alkyl group which may have a halogen atom or an aryl group as a substituent, or an aryl group which may have a halogen atom or an alkyl group having 1 to 6 carbon atoms as a substituent; $X_2$ is an oxygen atom or a sulfur atom; i is an integer of 0 to 4; and j is an integer of 0 to 3), or a group shown by the general formula [3]:

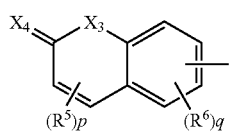

[3]

(wherein $R^5$ and $R^6$ are each independently a halogen atom, an alkyl group which may have a halogen atom or an aryl group as a substituent, or an aryl group which may have a halogen atom or an alkyl group having 1 to 6 carbon atoms as a substituent; $X_3$ and $X_4$ are each independently an oxygen atom or a sulfur atom; p is an integer of 0 to 2; and q is an integer of 0 to 3); $R^1$ and $R^2$ are each independently a halogen atom, an alkyl group which may have a halogen atom or an aryl group as a substituent, or an aryl group which may have a halogen atom or an alkyl group having 1 to 6 carbon atoms as a substituent; m and n are each independently an integer of 0 to 5; and $A_2$ is an anion derived from an inorganic strong acid, an organic acid or a compound shown by the general formula [4]:

[4]

(wherein $M_1$ is a boron atom or a gallium atom; and $R^7$ is an aryl group which may have a substituent selected from a haloalkyl group having 1 to 6 carbon atoms, a halogen atom, a nitro group and a cyano group)].

18. An acid generator according to claim 17, wherein the sulfonium salt shown by the general formula [9] is diphenyl (xanthene-9-one-2-yl)sulfonium hexafluorophosphate or (coumarin-7-yl)diphenylsulfonium hexafluorophosphate.

* * * * *